United States Patent
Von Drasek et al.

(10) Patent No.: US 10,598,574 B2
(45) Date of Patent: Mar. 24, 2020

(54) CONTROL OF INDUSTRIAL WATER TREATMENT VIA DIGITAL IMAGING

(71) Applicant: Ecolab USA Inc., St. Paul, MN (US)

(72) Inventors: William A. Von Drasek, Oak Forest, IL (US); Xuejun Wang, Oswego, IL (US)

(73) Assignee: Ecolab USA Inc., Saint Paul, MN (US)

( * ) Notice: Subject to any disclaimer, the term of this patent is extended or adjusted under 35 U.S.C. 154(b) by 311 days.

(21) Appl. No.: 15/654,003

(22) Filed: Jul. 19, 2017

(65) Prior Publication Data

US 2018/0024031 A1 Jan. 25, 2018

Related U.S. Application Data

(60) Provisional application No. 62/364,130, filed on Jul. 19, 2016.

(51) Int. Cl.
| | |
|---|---|
| *G01N 1/40* | (2006.01) |
| *G01N 17/00* | (2006.01) |
| *G01N 17/04* | (2006.01) |
| *G01J 3/28* | (2006.01) |
| *G01N 21/75* | (2006.01) |

(Continued)

(52) U.S. Cl.
CPC .............. *G01N 1/40* (2013.01); *G01J 3/2823* (2013.01); *G01N 17/006* (2013.01); *G01N 17/043* (2013.01); *G01N 21/75* (2013.01); *A61B 5/00* (2013.01); *G01J 3/00* (2013.01)

(58) Field of Classification Search
CPC ...... G01N 1/40; G01N 17/043; G01N 17/006; G01N 21/75; G01J 3/2823; G01J 3/00; A61B 5/00
See application file for complete search history.

(56) References Cited

U.S. PATENT DOCUMENTS

| 4,836,146 A | 6/1989 | Russell et al. |
|---|---|---|
| 5,174,654 A | 12/1992 | Droege |

(Continued)

FOREIGN PATENT DOCUMENTS

| JP | 3181543 B2 | 7/2001 |
|---|---|---|
| WO | WO 2005/085804 A1 | 9/2005 |
| WO | 2011018592 A1 | 2/2011 |

OTHER PUBLICATIONS

Choi et al., "Morphological analysis and classification of types of surface corrosion damage by digital image processing," *Corrosion Science*, 47, pp. 1-15 (2005).

(Continued)

*Primary Examiner* — Qian Yang
(74) *Attorney, Agent, or Firm* — Fredrikson & Byron, P.A.

(57) ABSTRACT

A method of analyzing a substrate contacting a fluid present in an industrial system is provided. The method comprises creating a series of digital images of the substrate while contacting the fluid present in the industrial system. A region of interest in the series of digital images of the substrate is defined. A corrosion feature in the region of interest in the series of digital images of the substrate is identified. The corrosion feature in the region of interest in the series of digital images of the substrate is analyzed to determine a corrosion trend of the industrial system. In certain embodiments of the method, the fluid is industrial water, and the industrial system is an industrial water system.

20 Claims, 17 Drawing Sheets

(51) Int. Cl.
*A61B 5/00* (2006.01)
*G01J 3/00* (2006.01)

(56) References Cited

U.S. PATENT DOCUMENTS

| | | | |
|---|---|---|---|
| 5,248,198 | A | 9/1993 | Droege |
| 5,278,074 | A | 1/1994 | Rao et al. |
| 5,320,779 | A | 6/1994 | Fivizzani |
| 5,332,900 | A | 7/1994 | Witzke et al. |
| 5,360,549 | A | 11/1994 | Mouche et al. |
| 5,399,017 | A | 3/1995 | Droege |
| 5,734,098 | A | 3/1998 | Kraus et al. |
| 5,750,070 | A | 5/1998 | Tang et al. |
| 5,992,505 | A | 11/1999 | Moon |
| 6,034,775 | A | 3/2000 | McFarland et al. |
| 6,068,012 | A | 5/2000 | Beardwood et al. |
| 6,143,800 | A | 11/2000 | Nguyen et al. |
| 6,250,140 | B1 | 6/2001 | Kouznetsov et al. |
| 6,336,058 | B1 | 1/2002 | Fowee |
| 6,375,829 | B1 | 4/2002 | Shevchenko et al. |
| 6,448,411 | B1 | 9/2002 | Meyer |
| 6,488,868 | B1 | 12/2002 | Meyer |
| 6,599,445 | B2 | 7/2003 | Meyer |
| 6,696,572 | B2 | 2/2004 | Meyer |
| 6,740,231 | B1 | 5/2004 | Bauman et al. |
| 6,792,357 | B2 | 9/2004 | Menon et al. |
| 6,942,782 | B2 | 9/2005 | Shevchenko et al. |
| 7,077,563 | B2 | 7/2006 | Xiao et al. |
| 7,135,683 | B2 | 11/2006 | Davis et al. |
| 7,563,377 | B1 | 7/2009 | Simpson |
| 7,842,127 | B2 | 11/2010 | Malwitz |
| 7,842,165 | B2 | 11/2010 | Shevchenko et al. |
| 8,585,930 | B2 | 11/2013 | Tiwari |
| 8,618,027 | B2 | 12/2013 | Meyer et al. |
| 8,945,371 | B2 | 2/2015 | Kouznetsov et al. |
| 8,959,898 | B2 | 2/2015 | Von Drasek et al. |
| 9,074,289 | B2 | 7/2015 | Malwitz et al. |
| 9,175,405 | B2 | 11/2015 | Gill et al. |
| 2005/0245411 | A1 | 11/2005 | Yang et al. |
| 2006/0241874 | A1* | 10/2006 | Carter .................. C02F 1/008 702/50 |
| 2006/0281191 | A1 | 12/2006 | Duggirala et al. |
| 2008/0308770 | A1 | 12/2008 | Tiwari |
| 2009/0158827 | A1 | 6/2009 | Dermody et al. |
| 2011/0274138 | A1 | 11/2011 | Auret et al. |
| 2011/0286492 | A1 | 11/2011 | Auret et al. |
| 2012/0073775 | A1 | 3/2012 | Duggirala et al. |
| 2012/0258547 | A1 | 10/2012 | Von Drasek et al. |
| 2014/0037037 | A1 | 2/2014 | Ito et al. |
| 2014/0177673 | A1 | 6/2014 | Bliss et al. |
| 2014/0272133 | A1 | 9/2014 | Gill et al. |
| 2014/0293040 | A1 | 10/2014 | Hietaniemi |
| 2014/0326667 | A1 | 11/2014 | Richmond et al. |
| 2014/0368823 | A1 | 12/2014 | Wirthlin et al. |
| 2016/0347716 | A1 | 12/2016 | Harbindu et al. |
| 2016/0348251 | A1 | 12/2016 | Seetharaman et al. |
| 2016/0348252 | A1 | 12/2016 | Rane et al. |
| 2016/0348253 | A1 | 12/2016 | Harbindu et al. |

OTHER PUBLICATIONS

Cicek et al., "Characterization Studies of Mild Steel Allow Substrate Surfaces Treated by Oxyanion Esters of [alpha]-Hydroxy Acids and Their Salts," *Int'l J. of Chemical Science and Tech.*, 2(3), pp. 244-260. (Oct. 1, 2012).

Fontana, "Table 4-5—Comparison of mils penetration per year (mpy) with equivalent metric-rate expressions," *Corrosion Engineering*, Third Edition, McGraw-Hill Book Company, New York, p. 172 (1986).

Garcia-Antón et al., "Online Visualization of Corrosion Processes of Zinc and a Cu/Zn Galvanic Pair in Lithium Bromide Solutions," *Corrosion*, 59(2), pp. 172-180 (Feb. 2003).

Isaacs et al., "Direct Image Processing of Corroding Surfaces Applied to Friction Stir Welding," BNL-72208-2004-CP, http://www.bnl.gov/isd/documents/26303.pdf, 7 pp. (2004).

Nalco, "ASTM G1-03—Standard Practice for Preparing, Cleaning, and Evaluating Corrosion Test Specimens," ASTM International, West Conshohocken, Pennsylvania, pp. 17-25 (2003).

Ott et al., "Modifications to the Copper Strip Corrosion Test for the Measurement of Sulfur-Related Corrosion," *J. of Sulfur Chem.*, 28(5), pp. 493-504 (Oct. 1, 2007).

Rivas et al., "Extreme value analysis applied to pitting corrosion experiments in low carbon steel: Comparison of block maxima and peak over threshold approaches," *Corrosion Science*, 50, pp. 3193-3204 (2008).

Sullivan et al., "In situ monitoring of the microstructural corrosion mechanisms of zinc-magnesium-aluminum alloys using time lapse microscopy," *Corrosion Science*, 53, pp. 2208-2215 (2011).

Van Der Merwe et al., "Comparison of Linear Polarization Resistance Corrosion Monitoring Probe Readings and Immersion Test Results for Typical Cooling Water Condition," *J. of the Southern African Inst. of Mining and Metallurgy*, 115, pp. 173-178 (Mar. 1, 2015).

European Patent Office, International Search Report in International Patent Application No. PCT/US2017/042783, 7 pp. (dated Dec. 13, 2017).

European Patent Office, Written Opinion in International Patent Application No. PCT/US2017/042783, 11 pp. (dated Dec. 13, 2017).

\* cited by examiner

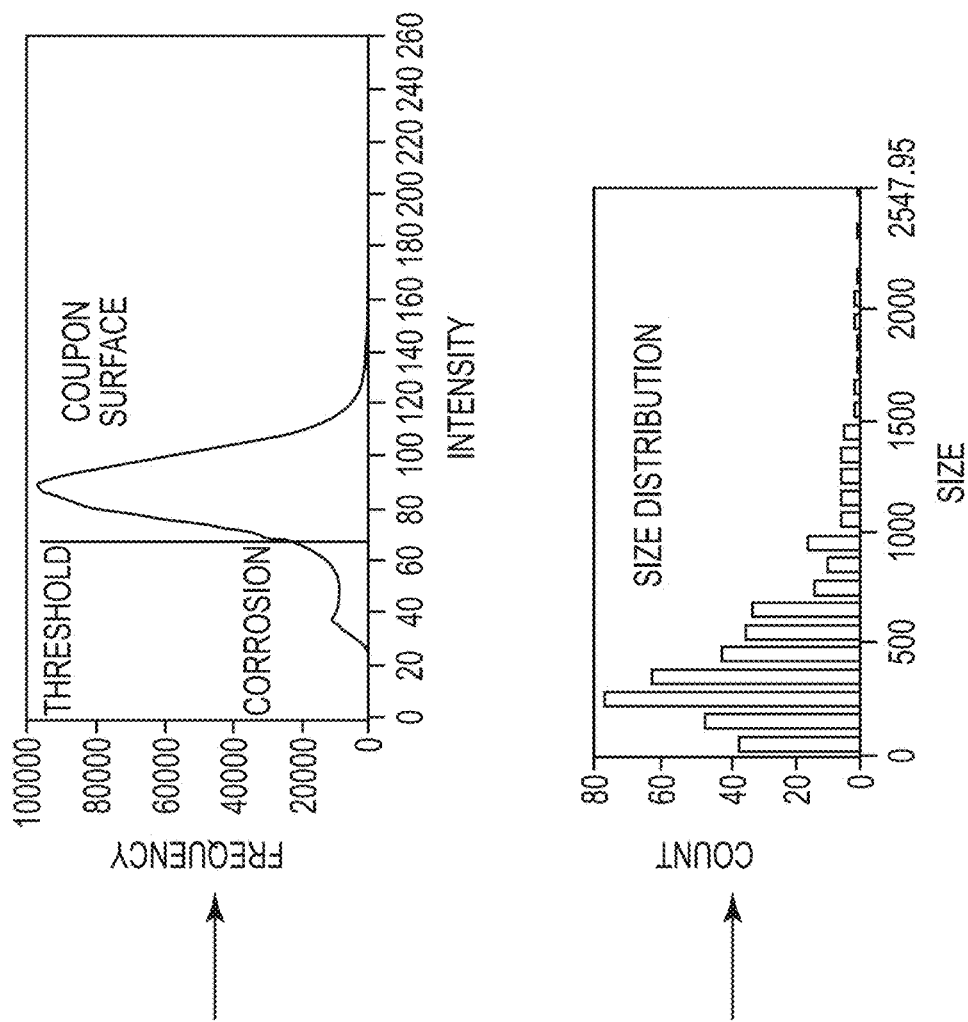
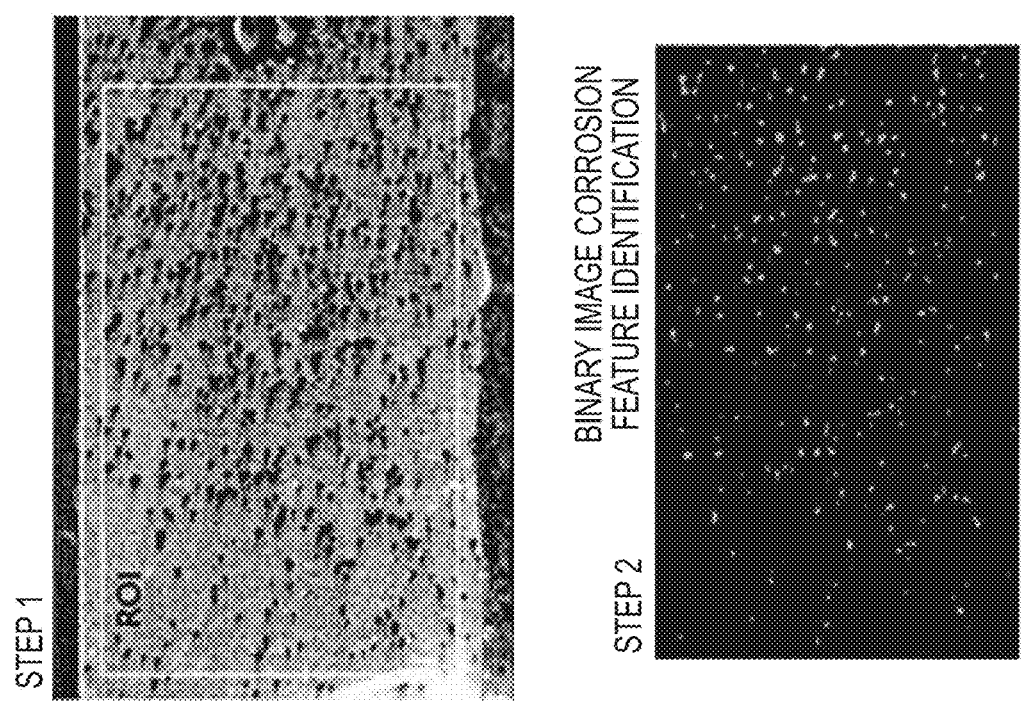
Fig. 8

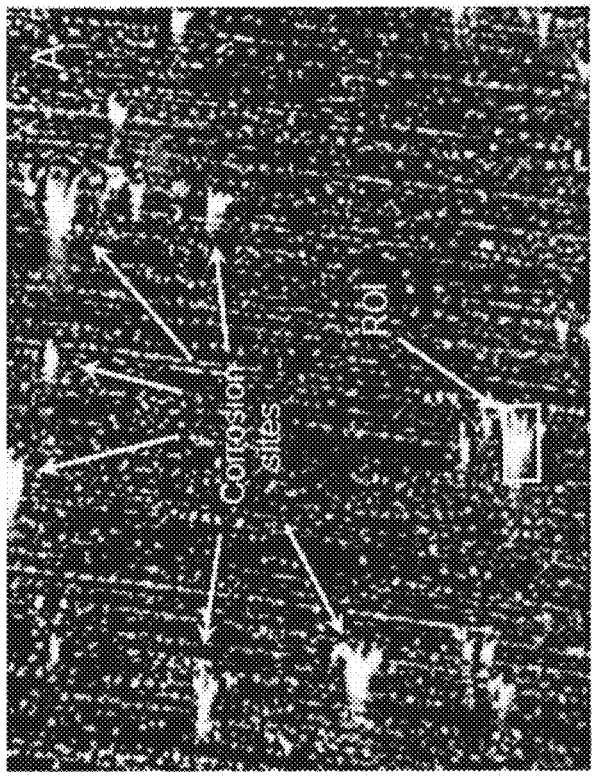
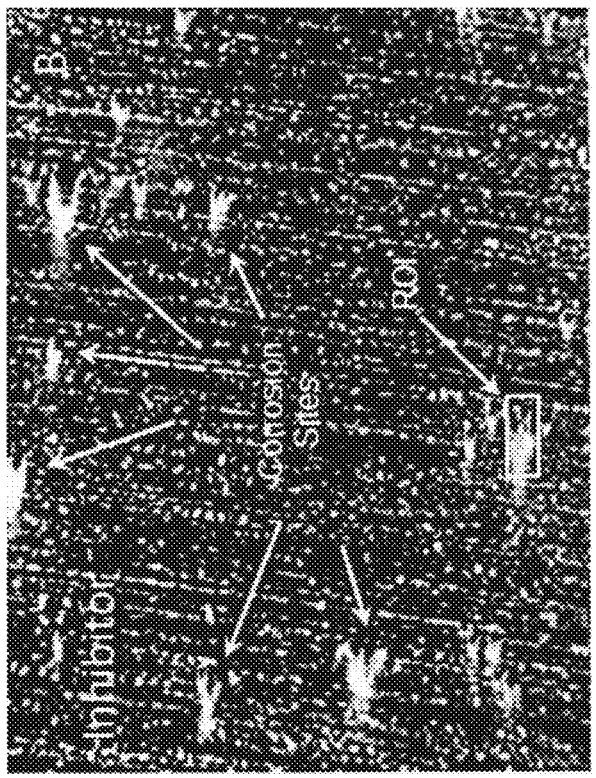
Fig. 16

CONTROL OF INDUSTRIAL WATER TREATMENT VIA DIGITAL IMAGING

This application is a nonprovisional application claiming the benefit of U.S. Provisional Patent Application Ser. No. 62/364,130, filed Jul. 19, 2016, the disclosure of which is incorporated herein by reference in its entirety.

BACKGROUND

Standard testing that utilize corrosion coupons can be used to measure general and local corrosion rates in industrial water systems. Standard testing involves placing an industry-standard corrosion coupon in a test space (e.g., an industrial water system) and allowing the corrosion coupon to be exposed to test space conditions, which may cause corrosion of the corrosion coupon. After a period of exposure time, generally 30-90 days or longer, the corrosion coupon is removed from the test space conditions. One or more of a series of tests is then performed to determine corrosion of the corrosion coupon, which generally corresponds to corrosion found on surfaces of the test space.

Standard testing using corrosion coupons has drawbacks. For example, "real-time" monitoring and analysis is not possible, as the corrosion coupon(s) are allowed to be exposed to test space conditions with little or no observation. Should the coupons be located so as to be observed, observation by the naked eye is subjective and generally not capable of observing subtle differences in coupons as the onset of corrosion begins to occur. Additionally, systems for detecting general corrosion typically lack the ability to detect or predict localized corrosion.

SUMMARY

The invention is directed to using digital imaging of a substrate to analyze for corrosion in an industrial system, which in certain embodiments is an industrial water system.

A method of analyzing a substrate contacting fluid present in an industrial system is provided. The method comprises creating a digital image of the substrate while the substrate contacts the fluid present in the industrial system. A region of interest in the digital image of the substrate is defined. A corrosion feature in the region of interest in the digital image of the substrate is identified. The corrosion feature in the region of interest in the digital image of the substrate is analyzed.

A method of analyzing a substrate contacting fluid present in an industrial system is provided. The method comprises creating a series of digital images of the substrate while the substrate contacts the fluid present in the industrial system. A region of interest in the series of digital images of the substrate is defined. A corrosion feature in the region of interest in the series of digital images of the substrate is identified. The corrosion feature in the region of interest in the series of digital images of the substrate is analyzed to determine a corrosion trend of the industrial system.

A method of analyzing a substrate contacting industrial water present in an industrial water system is provided. The method comprises treating the industrial water of the industrial water system with a corrosion inhibitor. A series of digital images of the substrate is created while the substrate contacts the industrial water present in the industrial water system. A region of interest in the series of digital images of the substrate is defined. A corrosion feature in the region of interest in the series of digital images of the substrate is identified. The corrosion feature in the region of interest in the series of digital images of the substrate is analyzed to determine a corrosion trend of the industrial water system, and taking action based on the analysis of the corrosion feature in the region of interest in the series of digital images of the substrate.

BRIEF DESCRIPTION OF THE SEVERAL VIEWS OF THE DRAWINGS

FIG. 8 shows examples of images subject to a method described herein.

FIG. 16 shows examples of images subject to a method described herein, which points out certain features of the imaged substrate.

DETAILED DESCRIPTION

Figure 1:
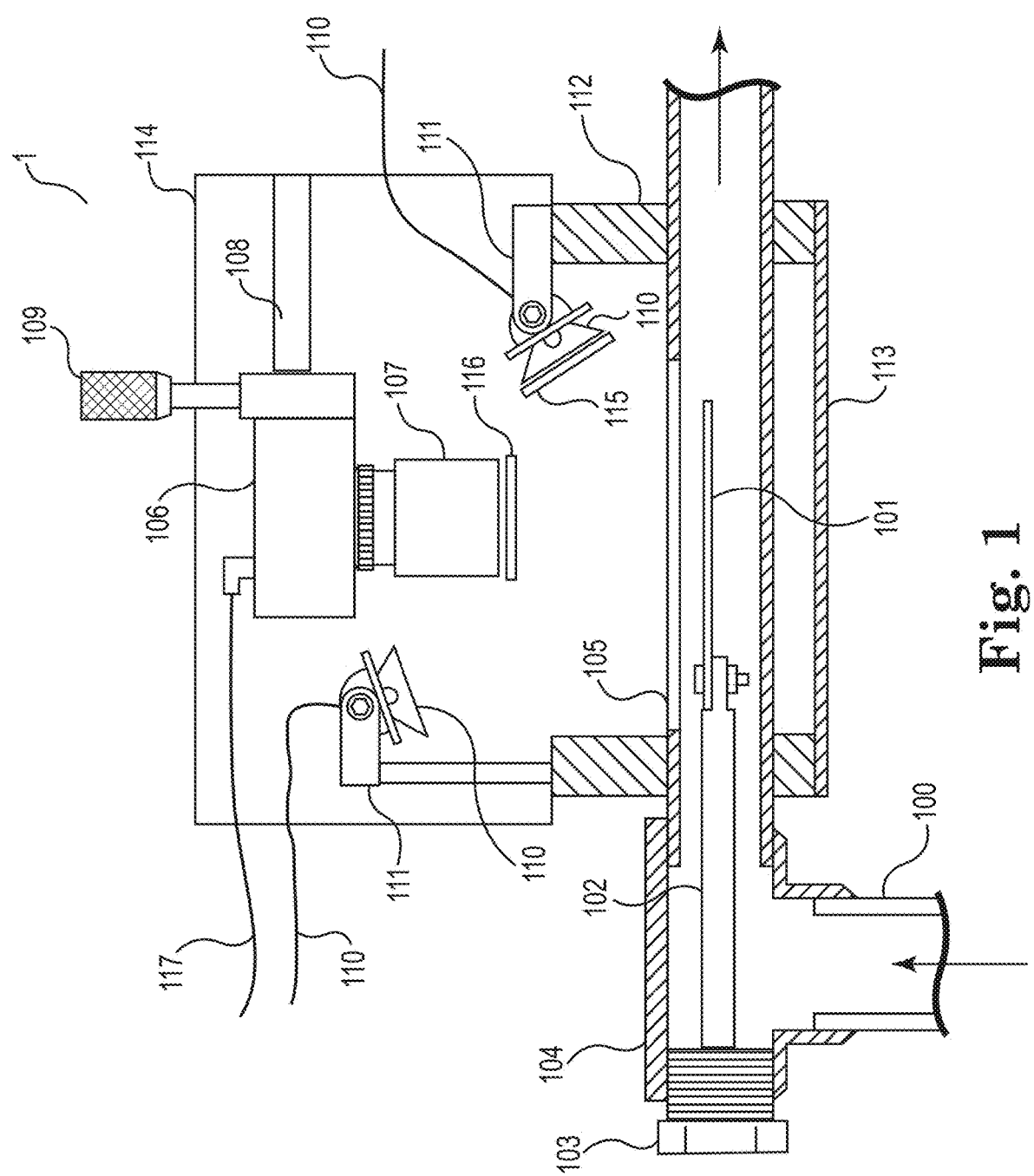
FIG. 1 is a schematic view of an embodiment of a system that may be utilized to carry out methods described herein.

A method of analyzing a substrate contacting fluid present in an industrial system is provided. The method comprises creating a digital image of the substrate while the substrate contacts the fluid present in the industrial system. A region of interest in the digital image of the substrate is defined. A corrosion feature in the region of interest in the digital image of the substrate is identified. The corrosion feature in the region of interest in the digital image of the substrate is analyzed.

A method of analyzing a substrate contacting a fluid present in an industrial system is provided. The method comprises creating a series of digital images of the substrate while contacting the fluid present in the industrial system. A region of interest in the series of digital images of the substrate is defined. A corrosion feature in the region of interest in the series of digital images of the substrate is identified. The corrosion feature in the region of interest in the series of digital images of the substrate is analyzed to determine a corrosion trend of the industrial system. In certain embodiments of the method, the fluid is industrial water, and the industrial system is an industrial water system.

In a preferred embodiment, the method is a method of analyzing a substrate contacting industrial water in an industrial water system. In certain embodiments, the method is a method of quantifying corrosion of a substrate contacting industrial water in an industrial water system. The phrases "analyzing a substrate," "defining a region of interest," "synthesizing trend data," and "quantifying corrosion of a substrate," and related terminology (e.g., conjugate forms), are used herein to describe aspects of the methods, with "analyzing a substrate" being inclusive of "quantifying corrosion of a substrate," "defining a region of interest," and "synthesizing trend data," which are all subsets of analyzing. The term "substrate," "corrosion coupon," and similar terms are to be construed as including "or a portion thereof."

In certain embodiments of the methods and systems provided herein, the substrate is a corrosion coupon. In certain embodiments of the methods and systems provided herein, the substrate is a section of a conduit. In certain embodiments of the methods and systems provided herein, the corrosion coupon is representative of a material of construction of the industrial water system. In certain embodiments of the methods and systems provided herein, the substrate, e.g., corrosion coupon, is constructed of a metal, which may be selected from steel, iron, aluminum, copper, brass, nickel, titanium, and related alloys. The steel may be mild steel, stainless steel, or carbon steel. In certain embodiments, the brass is admiralty brass. In certain embodiments, the metal is capable of passivation, and in other embodiments the metal is incapable of passivation.

In certain embodiments of the methods and systems provided herein, the substrate (e.g., a corrosion coupon) is capable of undergoing a standard corrosion test, e.g., a corrosion test of the American Society of Testing and Materials ("ASTM").

In a preferred embodiment of the methods provided herein, the substrate contacts industrial water present in an industrial water system. Examples of industrial water systems include, but are not limited to, heating water systems (e.g., boiler systems), cooling water systems (e.g., systems comprising a cooling tower), pipelines for water transport (e.g., seawater transport, which may be in transport to mining operations), and the like. Industrial water is any aqueous substance that is or will be used in an industrial water system. Generally, industrial water systems comprise industrial water that may be treated in some manner to make the water more suitable for use in the industrial water system of interest. For example, industrial water used in heating water systems (e.g., boiler systems) may be deaerated. The industrial water used in heating water systems may be further treated with a corrosion inhibitor. Other treatments may be rendered for various industrial water systems. In certain embodiments of the methods provided herein, the industrial water of the industrial water system is treated with a corrosion inhibitor. In certain embodiments of the methods provided herein, the industrial water system is a heating water system, which may be a boiler system. In certain embodiments of the methods provided herein, the industrial water of the heating water system has been deaerated.

Generally, industrial water is present in an industrial water system when the industrial water is contained or otherwise flowing through a conduit or vessel of the industrial water system. For example, industrial water flowing through a conduit attached to an industrial process (e.g., a cooling system, a boiler system, etc.)—whether the conduit be, e.g., a main line conduit, a side stream conduit, a feed line conduit, or an exit line conduit, and so forth—represents industrial water present in an industrial water system.

Examples of suitable corrosion inhibitors include, but are not limited to, an azole, a quaternized substituted diethylamino composition, an amine, a quaternary amine, an unsaturated aldehyde, a phosphorus-based inhibitor composition, a water-soluble molybdenum-containing salt, a poly (amino acid) polymer, an organic sulfonic acid, derivatives thereof (e.g., oxazole, thiazole, etc.), multiples thereof (e.g., more than one azole), and combinations thereof. In certain embodiments presented herein, the corrosion inhibitor, in addition to comprising one or more of the compositions listed in the previous sentence, further comprises an iodide salt. Examples of suitable iodide salts include, but are not limited to, lithium iodide, sodium iodide, potassium iodide, calcium iodide, magnesium iodide, ammonium iodide, tetraethylammonium iodide, tetrapropylammonium iodide, tetrabutylammonium iodide, tetrapentylammonium iodide, tetrahexylammonium iodide, tetraheptylammonium iodide, tetraphenylammonium iodide, phenyltrimethylammonium iodide and (ethyl)triphenylphosphonium iodide. In certain embodiments presented herein, the corrosion inhibitor is dosed to the industrial water of the industrial water system in an organic solvent and optionally a surfactant.

Further examples of corrosion inhibitors are described in U.S. Pat. Nos. 9,175,405, 9,074,289, 8,618,027, 8,585,930, 7,842,127, 6,740,231, 6,696,572, 6,599,445, 6,488,868, 6,448,411, 6,336,058, 5,750,070, 5,320,779, and 5,278,074; U.S. Pat. App. Pub. Nos. 2005/0245411 and 2008/0308770; and U.S. Prov. Pat. App. Nos. 62/167,658, 62/167,697, 62/167,710, and 62/167,719, the disclosures of each of which are incorporated herein by reference in their entirety for all purposes.

Examples of suitable azoles include, but are not limited to, azole-containing compositions, azoline-containing compositions, derivatives thereof (e.g., oxazoles, thiazoles, acridines, cinnolines, quinoxazolines, pyridazines, pyrimidines, quinazolines, quinolines, isoquinolines, etc.), multiples thereof, and combinations thereof. As it relates to this disclosure, another way to describe an azole is a composition having an aromatic, nitrogen-containing ring. Examples of azole-containing compositions include, but are not limited to, imidazoles, pyrazoles, tetrazoles, triazoles, and the like. Particularly suitable azoles include, e.g., mercapto-benzothiazole ("MBT"), benzotriazole ("BT" or "BZT"), butyl-benzotriazole ("BBT"), tolytriazole ("TT"), naphthotriazole ("NTA"), and related compositions. Examples of azoline-containing compositions include, but are not limited to, imino imidazolines, amido imidazolines, derivatives thereof, multiples thereof, and combinations thereof. In certain embodiments presented herein, the azole is quaternized. Examples of azoles are described in further detail in U.S. Pat. Nos. 5,278,074, 6,448,411, and 8,585,930, which have been incorporated herein by reference.

Examples of suitable substituted diethylamino composition include, but are not limited to, those described in U.S. Pat. Nos. 6,488,868, 6,599,445, and 6,696,572, which have been incorporated herein by reference. In certain embodiments presented herein, the substituted diethylamino composition is quaternized. The substituted diethylamino composition may also be an azole, e.g., a quaternized diacrylamino imidazoline.

Examples of suitable amines (whether quaternized or otherwise) include, but are not limited to, those described in U.S. Pat. Nos. 7,842,127, 8,618,027, which have been incorporated herein by reference.

Examples of suitable unsaturated aldehydes include, but are not limited to, those described in U.S. Pat. No. 7,842,127, which has been incorporated herein by reference.

Examples of suitable phosphorus-based inhibitor compositions include, but are not limited to, inorganic phosphorus-based inhibitor compositions, organic phosphorus-based inhibitor compositions, organophosphorus compositions, and combinations thereof. Examples of inorganic phosphorus-based inhibitor compositions include, but are not limited to, ADD, and combinations thereof. Examples of organic phosphorus-based inhibitor compositions include, but are not limited to, organic phosphates, organic phosphonates, and combinations thereof. Examples of organic phosphates include non-polymeric organic phosphates and polymeric organic phosphates. For purposes of this disclosure, "polymeric" describes a composition having repeating units, and "non-polymeric" describes a composition without repeating units. Examples of organic phosphonates include, but are not limited to, 2-phosphonobutane-1,2,4-tricarboxylic acid ("PBTC"), 1-hydroxyethylidene-1,1-diphosphonic acid ("HEDP"), aminotrimethylene-phosphonic acid, monosodium phosphinicobis (succinic acid), ADD. Examples of organophosphorus compositions include phosphines.

Examples of suitable organic sulfonic acids include, but are not limited to, those described in U.S. Pat. No. 8,618,027, which has been incorporated herein by reference. Examples of suitable organic sulfonic acids include, but are not limited to, benzenesulfonic acid, dodecylbenzenesulfonic acid ("DDBSA"), and preferably branched DDBSA.

Examples of suitable water-soluble molybdenum-containing salts include, but are not limited to, alkali molybdates, e.g., sodium molybdate, potassium molybdate, ammonium molybdate, strontium molybdate, and the like.

In certain embodiments, the poly(amino acid) polymer has a hydroxamic acid-containing sidechain. An example of a suitable poly(amino acid) polymer having a hydroxamic acid-containing sidechain includes, but is not limited to, that of general Formula (I):

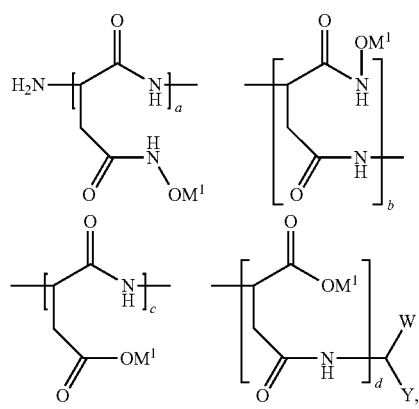

(I)

wherein W is $CO_2M^x$ or CONHOH, wherein $M^x$ is a metal ion; Y is $CH_2CONHOH$ or $CH_2CO_2M^y$, wherein $M^y$ is the same or different metal ion as $M^x$; $M^1$ is an alkali metal, an alkaline earth metal or ammonium; $(a+b)/(a+b+c+d)*100\%+(c+d)/(a+b+c+d)*100\%=100\%$ ranges from about 0.1% to about 100%, preferred 5%-70%, more preferred 10%-50%; $(c+d)/(a+b+c+d)*100\%$ ranges from 0% to 99.9%; $a/(a+b)*100\%$ ranges from 0% to 100%; $b/(a+b)*100\%$ ranges from 0% to 100%; $a/(a+b)*100\%+b/(a+b)*100\%=100\%$; $c/(c+d)*100\%$ ranges from 0% to 100%; $d/(c+d)*100\%$ ranges from 0% to 100%; $c/(c+d)*100\%+d/(c+d)*100\%=100\%$; and the molecular weight ranges from about 300 to about 200,000 daltons. Further examples of suitable poly(amino acid) polymers having a hydroxamic acid-containing sidechain are described in U.S. Pat. No. 5,750,070, which has been incorporated by reference.

The corrosion inhibitor may be present in the industrial water at a concentration of from about 0.01 ppm to about 1000 ppm by weight, including from about 0.1 ppm or from about 1 ppm, to about 500 ppm, or to about 200 ppm.

In certain embodiments of the methods provided herein, a parameter of the industrial water system is measured. Parameters include, but are not limited to, temperature, pressure, pH, conductivity, oxidation-reduction potential, linear polarization resistance, derivatives thereof, and combinations thereof. In a preferred embodiment, the methods described herein further comprise measuring linear polarization resistance of the fluid in the industrial system, and acting based on at least one of the analysis of the corrosion feature in the region of interest of the digital image, or series thereof, of the substrate, and the measured linear polarization resistance of the fluid of the industrial system. In a preferred embodiment, the invention is directed to using digital imaging of a substrate and linear polarization resistance to analyze for corrosion in an industrial water system.

The substrate is sufficiently lit to allow for creation of digital images of the substrate located in the industrial water system. In preferred embodiments, the substrate is sufficiently lit using a light-emitting diode, and, more preferably, a plurality of light-emitting diodes.

In certain embodiments of the methods disclosed herein, a series of digital images of the substrate is created. In certain preferred embodiments, the series of digital images of the substrate is created while the substrate is located in an industrial system, e.g., an industrial water system. Though not preferred, the series of digital images of the substrate can be created while the substrate is not located in an industrial system. In the preferred embodiments, the substrate located in the industrial system, e.g., an industrial water system, is generally in contact with a fluid, e.g., industrial water.

When utilized, the series of digital images may be two or more digital images. In certain embodiments of the methods provided herein, the series of digital images comprises a quantity of digital images sufficient to perform trend analysis of the digital images, and thus of the substrate. In preferred embodiments of the methods provided herein, the series of digital images is a quantity sufficient to perform corrosion trend analysis of the substrate. In certain embodiments of the methods provided herein, the series of digital images is created at a fixed time interval, i.e., each image is taken after a fixed amount of time has elapsed. In certain embodiments of the methods provided herein, the series of digital images is created at a fixed time interval when a parameter of the industrial system, e.g., industrial water system, is within a control limit, but the series of digital images is created at an interval of time less than the fixed time interval when the parameter of the industrial system is not within the control limit. In other words, when the process is in control, a digital image is created at a rate of one digital image per t-length of time, but when the process is out of control, a digital image is created at a rate faster than one digital image per t-length of time.

In certain embodiments of the methods provided herein, the digital image, or series thereof, of the substrate is analyzed to determine a corrosion trend of the substrate in the industrial system, e.g., industrial water system. In certain embodiments, analyzing comprises defining a region of interest in the series of digital images of the substrate and synthesizing trend data of the region of interest from the series of images. In some embodiments, analyzing comprises mathematical transformation of data to synthesize information related to size (e.g., a one-dimensional measurement or surface area calculation to infer pit depth), color profile, number of corrosion features, percent area covered by corrosion features, overall mean surface area of corrosion features, percent active corrosion features, and combinations thereof, to calculate a corrosion trend (e.g., a localized corrosion rate). Localized corrosion and examples of mathematical transformations of data are discussed further herein. In certain embodiments of the methods provided herein, the method further comprises estimating pit depth of the corrosion feature based on the estimated surface area of the corrosion feature. In certain embodiments of the methods provided herein, the method further comprises estimating pit depth of the corrosion feature based on a one-dimensional measurement of the corrosion feature. Examples of one-dimensional measurements of a corrosion feature includes, but is not limited to, length (e.g., a point-to-point measurement across a corrosion feature), perimeter (e.g., circumference around a corrosion feature), and similar measurements and estimates thereof.

In certain embodiments, the methods comprise defining a region of interest in the digital image, or series thereof, of the substrate. The region of interest may comprise a surface of the substrate. In certain embodiments of the methods provided herein, the region of interest is a surface, or portion thereof, of a substrate (e.g., a corrosion coupon).

In certain embodiments of the methods provided herein, the region of interest comprises one or more corrosion features. In certain embodiments of the methods provided herein, a plurality of corrosion features is identified in the region of interest. The corrosion features may be counted and/or tracked for changes in number, which can provide information related to the corrosive environment that may be present in the industrial system, e.g., industrial water system. In certain embodiments, the method comprises identifying a corrosion feature in the region of interest, which may further comprise predicting a future corrosion event based on the corrosion feature. In certain embodiments of the methods provided herein, the surface area of the corrosion feature is calculated, which allows for a prediction of pit depth estimated based on the surface area of the corrosion feature.

Localized corrosion tends to form pits in material surfaces, and thus is sometimes called "pitting" corrosion. Localized corrosion can be described as a stochastic process with variable rates. Generally, localized corrosion is responsible for many industrial system failures, particularly related to industrial water systems. While general corrosion of industrial systems may be somewhat predictable using conventional corrosion monitoring (e.g., linear polarization resistance, ("LPR")), localized corrosion has been more difficult to monitor and/or predict in real time, generally requiring sophisticated instrumentation and analytical procedures. In certain embodiments of the methods provided herein, the corrosion trend determined for the industrial system is a localized corrosion trend.

In certain embodiments, a potential future corrosion event is predicted based on the analysis, or subsets thereof, of the series of digital images. In certain embodiments of the methods provided herein, the potential future corrosion event is any one or more of the following: corrosion rate, corrosion failure, and combinations thereof.

In certain embodiments of the methods provided herein, action is taken (i.e., "acting") based on the analysis of the corrosion feature in the region of interest of the digital image, or series thereof, of the substrate. Generally, the action taken will be one or more action to prevent or lessen the effects of corrosion (preferably localized corrosion) in the industrial system, e.g., an industrial water system. Any one or more actions may be taken, including, but not limited to, increasing dosage of corrosion inhibitor, selecting a different corrosion inhibitor, modifying the corrosion inhibitor, altering a physical property of the industrial system, shutting down the industrial system, and combinations thereof.

In certain embodiments of the methods provided herein, time scale and/or end-point measurement limitations of substrate monitoring are addressed by integrating an imaging system into the industrial system, e.g., an industrial water system. In certain embodiments of the methods provided herein, the substrate is a corrosion coupon, and the imaging system is integrated as part of a standard coupon rack. In certain embodiments of the methods provided herein, the imaging system is non-intrusive. In certain embodiments of the methods provided herein, the imaging system provides the ability to capture real-time corrosion activity on the surface of a coupon contacting a fluid (e.g., industrial water) present in an industrial system (e.g., an industrial water system. For example, FIG. 1 shows a portion of an industrial system, in this example, an industrial water system, comprising imaging system 1 attached to the industrial water system at a process flow pipe. The portion of the industrial water system comprises pipe 100 that transports a fluid, in this example, industrial water, to substrate 101 (e.g., a corrosion coupon) held in the pipe by substrate holder 102 connected to pass-through 103 inserted into tee 104. Substrate 101 may be constructed of a metal that is representative of the wetted materials of construction of the industrial water system being monitored, which in certain embodiments comprises carbon steel, brass (e.g., admiralty brass), stainless steel, aluminum and/or related alloys. Other selection options are that one or more surfaces of the substrate have a certain finish, e.g., ground, sand blasted, polished, etc., and whether or not the substrate is passivated. Components 100-104 may partially or entirely comprise standard coupon mounting hardware used in commercially available corrosion coupon racks (e.g., EnviroAqua Consultants Inc., 7116 Sophia Ave, Van Nuys, Calif., Model ACR-22) designed according to ASTM specifications.

The imaging system requires optical access to view the substrate contacting the process fluid stream, i.e., the industrial water. Generally, commercial coupon rack systems use clear PVC pipe to provide operators the ability to visually inspect a corrosion coupon, which allows for direct mounting of the imaging system. If the pipe is opaque, then modifications are required such as installing a clear PVC pipe section or modifying the pipe to provide optical access. FIG. 1 shows optical access as window 105.

Figure 2:
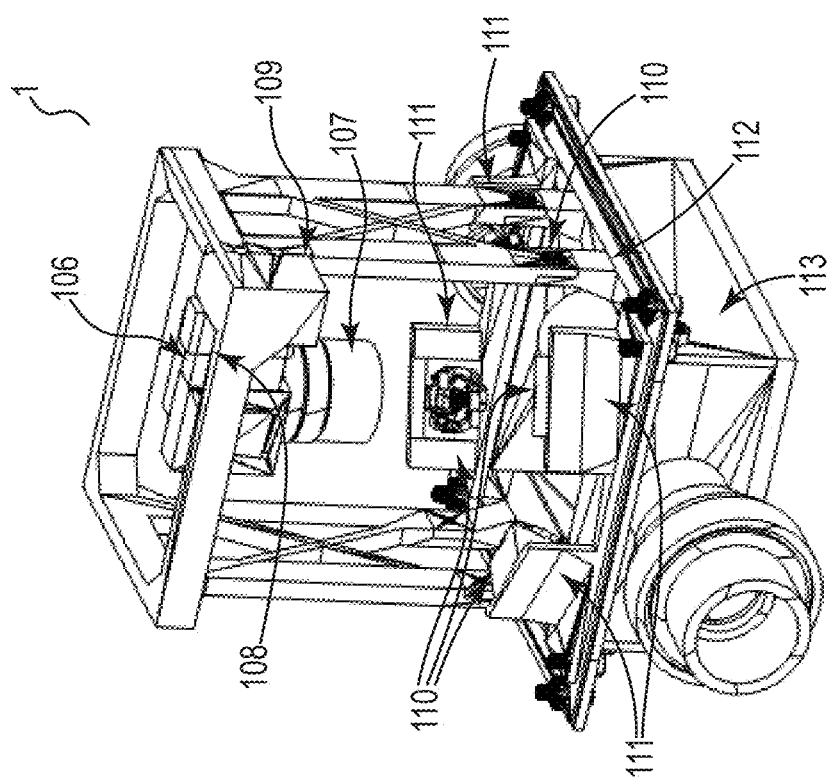
FIG. 2 is a schematic view of an alternate embodiment of a system that may be utilized to carry out methods described herein.

FIG. 2 shows an alternate embodiment of imaging system 1, which includes many of the same features as the embodiment illustrated in FIG. 1. For example, the imaging systems of FIGS. 1 and 2 comprise camera 106, which may be a complementary metal-oxide-semiconductor ("CMOS") or a charge-coupled device ("CCD") camera, equipped with lens 107. In the embodiments of FIGS. 1 and 2, camera 106 is mounted on fixture 108 via linear translation stage 109, which allows for adjustment of focus. Alternatively, a camera with an autofocus feature such as, e.g., The Imaging Source camera model DKF72AU02-F (6926 Shannon Willow Road, Charlotte, N.C. 28226) can be utilized, obviating the need for linear translation stage 109. Camera 106 can be black and white or preferably color to provide additional insight into corrosion dynamics. In the embodiments of FIGS. 1 and 2, light sources 110 are used to illuminate the coupon, which may not be necessary depending on natural and/or other artificial light available at any particular location.

Multiple light sources may be used to illuminate from different direction to accentuate the desired features on the substrate or surface thereof, or to improve the overall illumination profile. For example, illuminating a surface of the substrate with a light source positioned near perpendicular to the surface can provide a bright field illumination. In this case, the imaging device captures most of the direct reflected light. Placing one or more light sources with large angle(s) of incidence relative to the surface normal can enhance salient features, such as scratches or pits, on the surface. In addition, the light can be directional or diffuse. Diffuse lighting provides more uniform illumination and attenuates the specular component when illuminating reflective surfaces. The light may be sourced from one or more of a light emitting diode ("LED"), an incandescent bulb, a tungsten halogen bulb, light transported via fiber optic or any combination of these or other standard means to provide illumination. In certain embodiments of the systems and methods provided herein, four LED light sources are utilized and arranged such that each of the four LED light sources directs light in an X pattern toward the substrate, an example of which is shown in FIG. 2.

An example of an LED light source is available as CREEXPE2-750-1 from Cree, Inc., 4600 Silicon Drive Durham, N.C. 27703, which in certain embodiments is equipped with a Carclo lens model 10138, available from Carclo Optics, 6-7 Faraday Road, Rabans Lane Industrial Area, Aylesbury HP19 8RY, England, U.K.

In the embodiments of FIGS. 1 and 2, light sources 110 are mounted to mounts 111 that allow for angle and height adjustment. The light emission wavelength spectrum can cover the white light region or specific wavelength bands to highlight specific features. For example, specific wavelengths can be used to highlight color on the substrate surface or used with black and white camera to extract color information from the surface. In certain embodiments of the methods presented herein, the substrate is lit with light having a wavelength band of from about 390 nm to about 700 nm.

Image acquisition control can be made by a PC, microprocessor, external controller, and/or embedded processor on the camera. Commercial digital cameras generally come standard with image acquisition speeds 30 frames per second ("fps") or greater. Because corrosion generally occurs at a much longer time scale (e.g., 10s of minutes to weeks), image acquisition control is the preferred method, i.e., acquiring a single image or average of N images at a frequency that can be, e.g., fixed, variable, and/or event driven. Collecting data in this manner utilizes data storage more efficiently. For example, an image acquisition rate of once per day, or once per week, may be sufficient for certain industrial systems if only gross changes in corrosion features are of interest. However, if the industrial system experiences an upset, e.g., a drop in pH, the dynamics of the corrosion features can be missed with infrequent image acquisition. In this case, triggering an increase in the frequency of the creation of the digital images at the time of upset allows for collecting image data at a finer time resolution.

Interfacing the imaging system to a fluid stream in an industrial system (e.g., to a stream of industrial water in an industrial water system) can be done by directly mounting the imaging system on a process pipe, as shown in FIGS. 1 and 2, using, e.g., mounting clamps 112. Bottom plate 113 and enclosure housing 114 provide protection to the internal components from the environment. Additionally, bottom plate 113 and enclosure housing 114 control ambient light from interfering with the light produced by light sources 110. Electrical power and/or communication can be provided to components of the imaging system by cabling connections and/or antennae.

Additional illumination control can be provided via the utilization of filters and/or polarizers on light source(s) 110 and/or imaging device 106. For example, adding linear polarizers 115 and 116 allows for the removal of reflections or hot spots (e.g., high light intensity glare) from the image originating from the light source rays that, e.g., may reflect off the transparent window or pipe. Additionally or instead, color filters (e.g., bandpass, notch, shortpass, and/or longpass) may be used to enhance specific image detail or remove background light effects. Filtering can be applied on the camera, light source, or both. For example, red features on a surface can be enhanced using a light source with a bandpass or longpass filter greater than 600 nm, e.g., 600-1100 nm, or more preferably 600-700 nm, and even more preferably, 630 nm. In this case, the red light will reflect off the red surfaces of the substrate to the imaging detection device that can also be equipped with a similar filter. This allows only the reflected light from the surface in the wavelength transmission range of the filter to reach the detector, resulting in red feature enhancement.

In certain embodiments, the methods provide the ability to monitor multiple locations of the substrate. For example, a plurality of cameras and light sources mounted at different positions relative to the substrate can provide the ability to image different sides, edges, and angles of the substrate (e.g., coupon).

Figure 3:
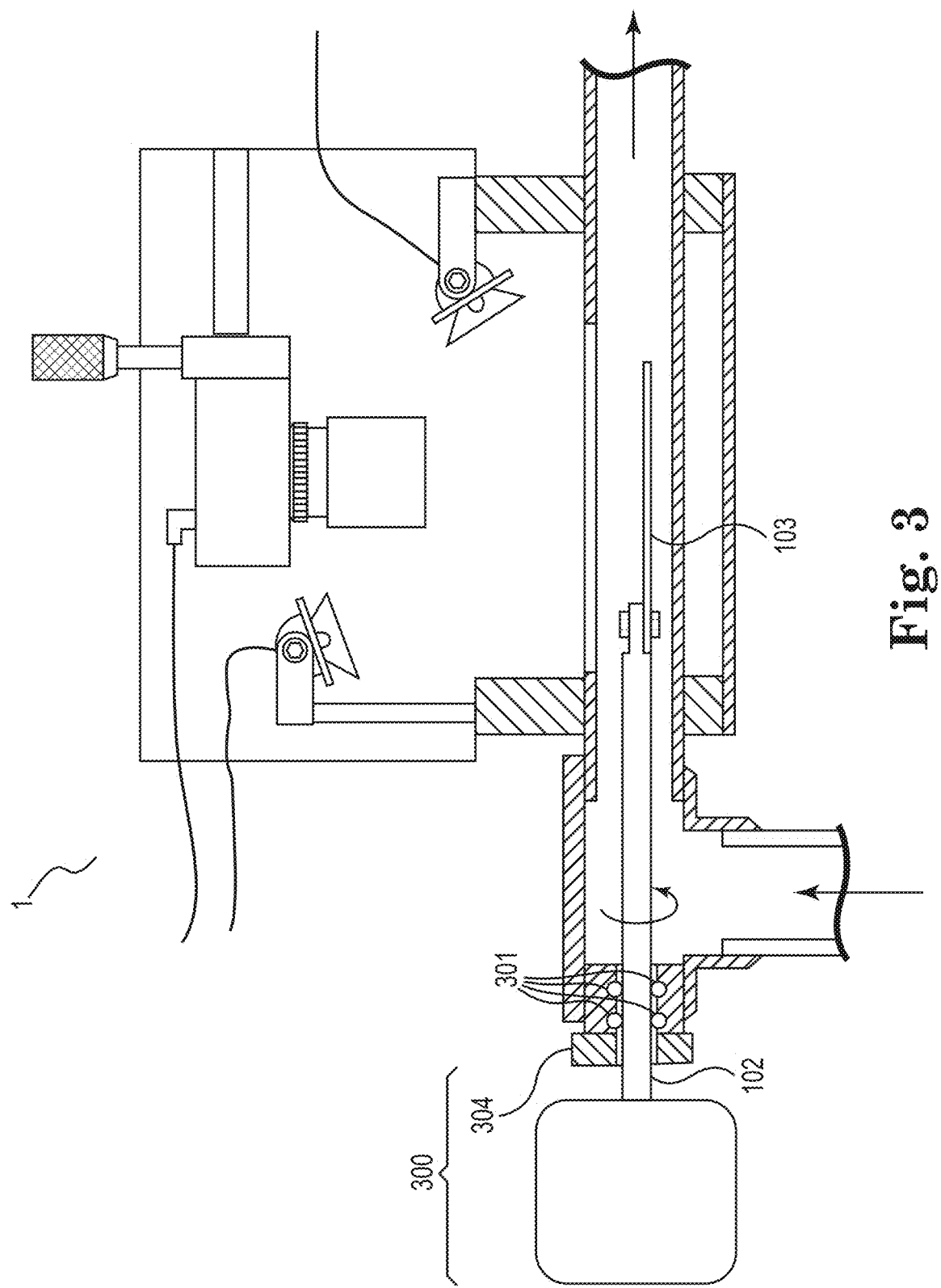
FIG. 3 shows an embodiment of a substrate positioning device that may be utilized in systems and methods described herein.

Alternatively, as shown in FIG. 3, substrate positioning device 300 may be utilized, which allows substrate 103 to be rotated to different positions to image both sides of the substrate (front and back) as well as a side and/or angled views. The system shown in FIG. 3 comprises substrate positioning device 300 attached to substrate holder 102 that is inserted through pass-through 304. Pass-through 304 uses seals 301 (e.g., O-rings) to provide a seal and allow substrate holder 102 to rotate. Otherwise, imaging system 1 of FIG. 2 is the same configuration as system 1 as shown in FIG. 1. Substrate positioning device 300 can be manual control, servomotor, or stepper type to control the coupon position.

Figure 4:
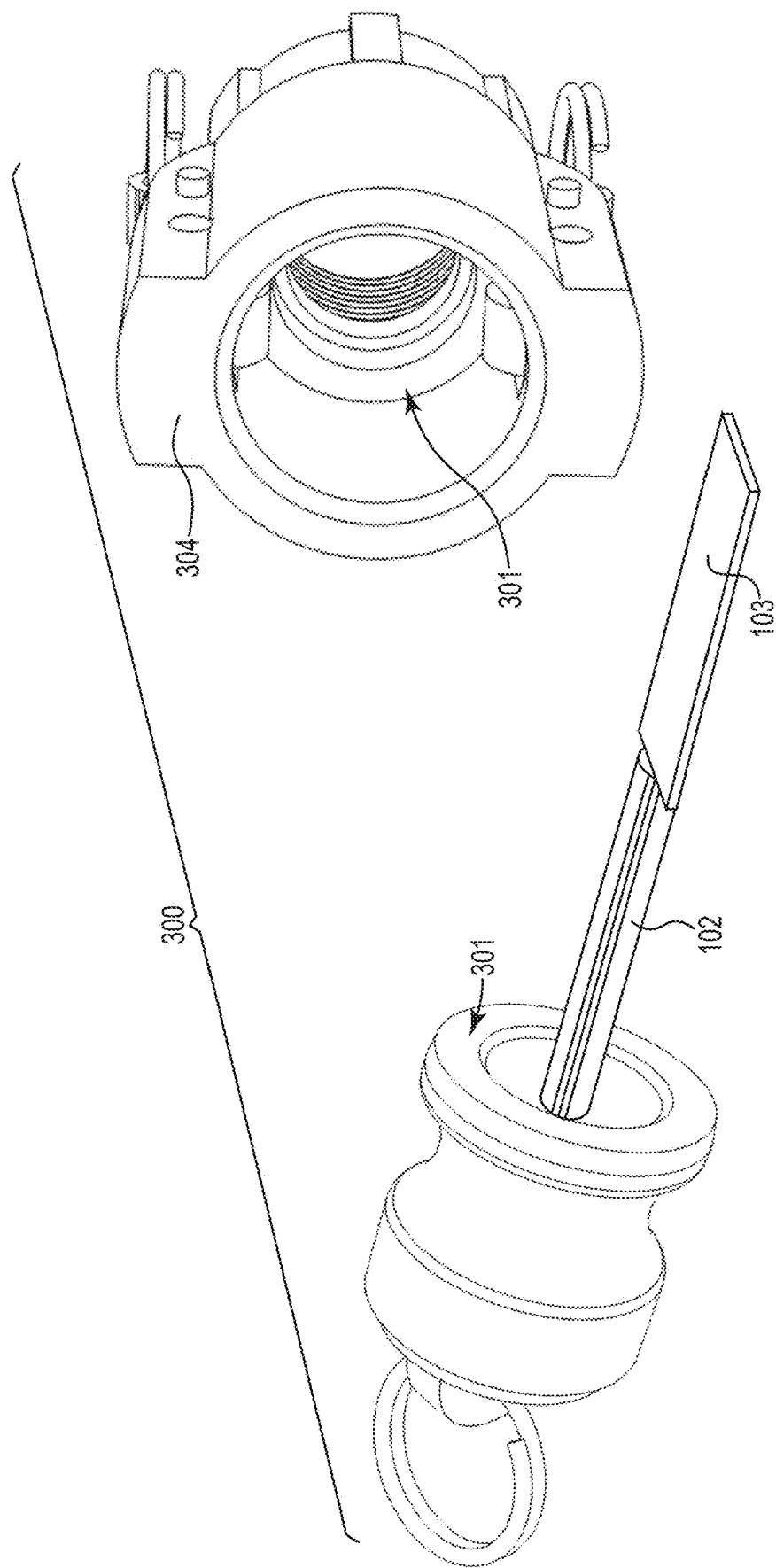
FIG. 4 is a schematic view of an alternate embodiment of a system that may be utilized to carry out methods described herein.

Another example of substrate positioning device 300 is shown in FIG. 4, which for this embodiment is constructed of a keyed plug modified to be attached to substrate holder 102, which attaches to substrate 103. Substrate holder 102 and substrate 103 are inserted through pass-through 304. Pass-through 304 uses one or more seals 301 to provide a seal and allow substrate holder 102 to rotate. Like in the embodiment of FIG. 3, substrate positioning device 300 of FIG. 4 can be manual control, servomotor, or stepper type to control the coupon position. The substrate positioning devices of FIGS. 3 and 4 may be utilized as part of the systems of either of FIGS. 1 and 2.

Figure 5:
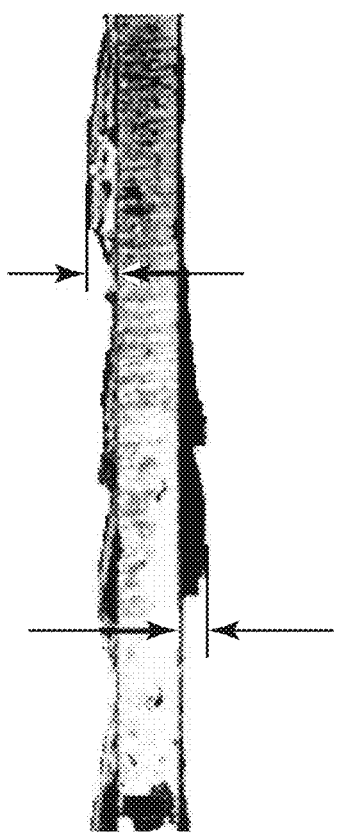
FIG. 5 shows an image of a series of images of an edge view of a substrate subject to a method described herein.

An example case where the substrate is imaged at a different position is shown in FIG. 5 for a side view of a mild steel coupon exposed to Water A for 22 days. Imaging the side of the coupon allows for the capture of details about the height (maximum height) of the corrosion products formed on the coupon surface. The magnitude of the height and monitoring the height change in time provides insight on the level of corrosion activity, e.g., a large change in height suggesting an increased level of corrosion activity.

Figure 6:
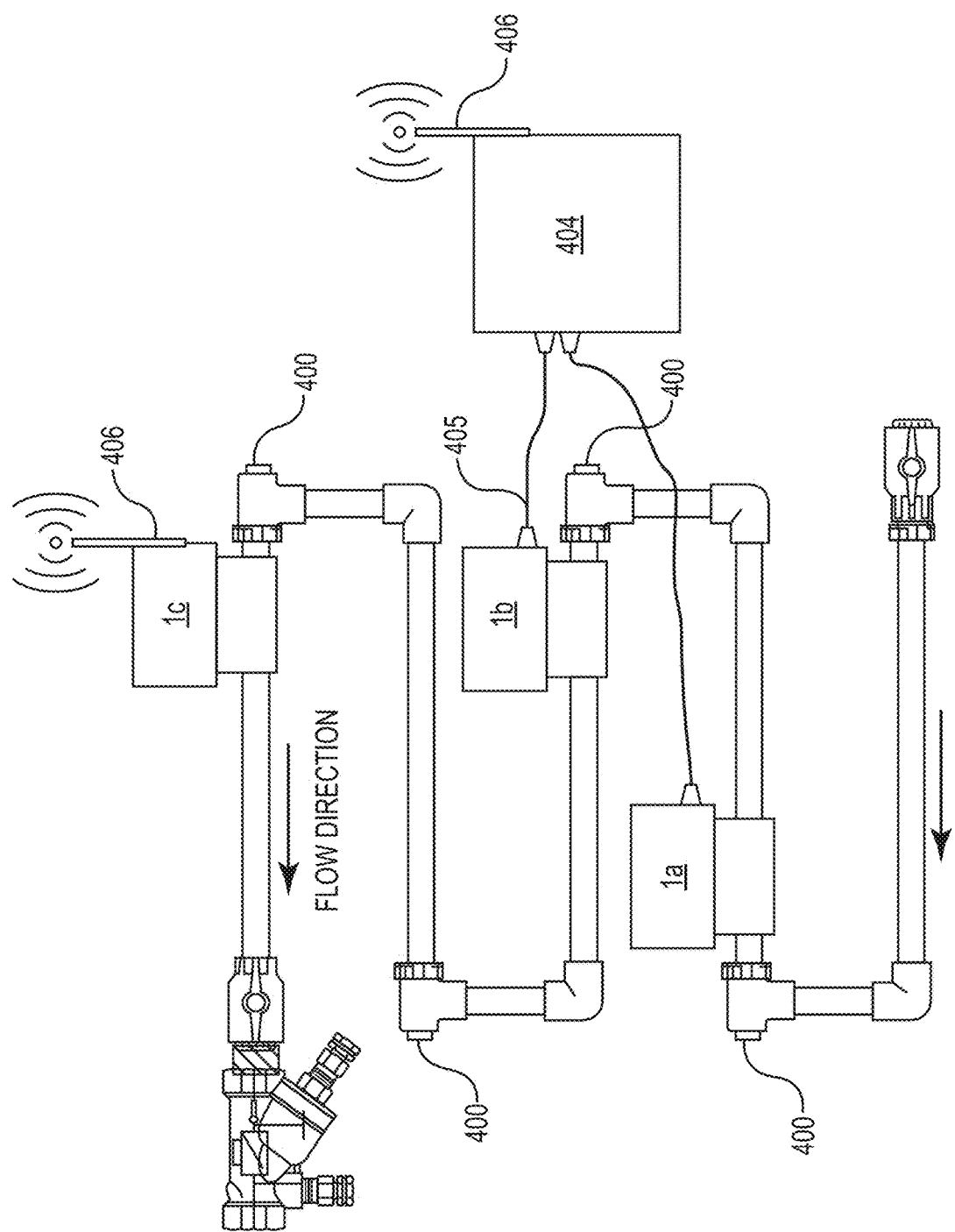
FIG. 6 is a schematic view of a system that may carry out the methods described herein.

In certain embodiments, a plurality of imaging devices is utilized to create a plurality of digital images, or series (plural) thereof, of one or more substrates. For example, multiple imaging systems can be mounted on an industrial water system to monitor at different points and/or varied substrate metallurgy. FIG. 6 shows an example of a coupon rack with 4 coupon mounting points 400 further comprising a coupon holder rod, holder nut, and coupon, though the substrate positioning devices of either of FIGS. 3 and 4 could be utilized. The coupon rack is outfitted with three imaging systems 1 (labeled 1a-1c to differentiate each from the others) as previously described and shown in FIGS. 1 and 2. The imaging systems interface directly to controller 404 that can be a PC, microprocessor, gateway, or combination of such devices to establish electronic communication for acquisition control as well as store and/or transmit image data. FIG. 6 shows cabling 405 connecting imaging systems 1a and 1b. In certain embodiments (e.g., imaging system 1a and 1b), cabling 205 provides power and bi-directional data transfer, i.e., collect image data or send commands to control digital camera settings. Alternatively, a wireless protocol (e.g., one or more of Wi-Fi, Zigbee, LoRa, Thread, BLE OnRamp, RPMA, the EEE 802.11 network family, IEEE 802.15.4, Bluetooth, HiperLAN, etc.) can be used to communicate between the imaging device and controller 404, as shown for imaging device 1c equipped with a wireless communication device communicates to controller 404 via antennae 406. Powering the imaging units can be through cable 405, battery, solar, or other energy harvesting means, e.g., vibration or thermal. The combination of using a wireless protocol with a self-powered method allows convenient installation at multiple locations. Image data collected by controller 404 can be stored, processed using advanced image analysis algorithms, processed and reduced to key trending variables, transmit data to a remote server, or communicate with a control device, e.g., a distributed control system ("DCS," e.g., Nalco 3D technology, available from Nalco Water, an Ecolab company, 1601 West Diehl Road, Naperville, Ill. 60563), a laboratory information management system (e.g., a "LIMS" software/hardware package), and/or a cloud computing system.

Figure 7:
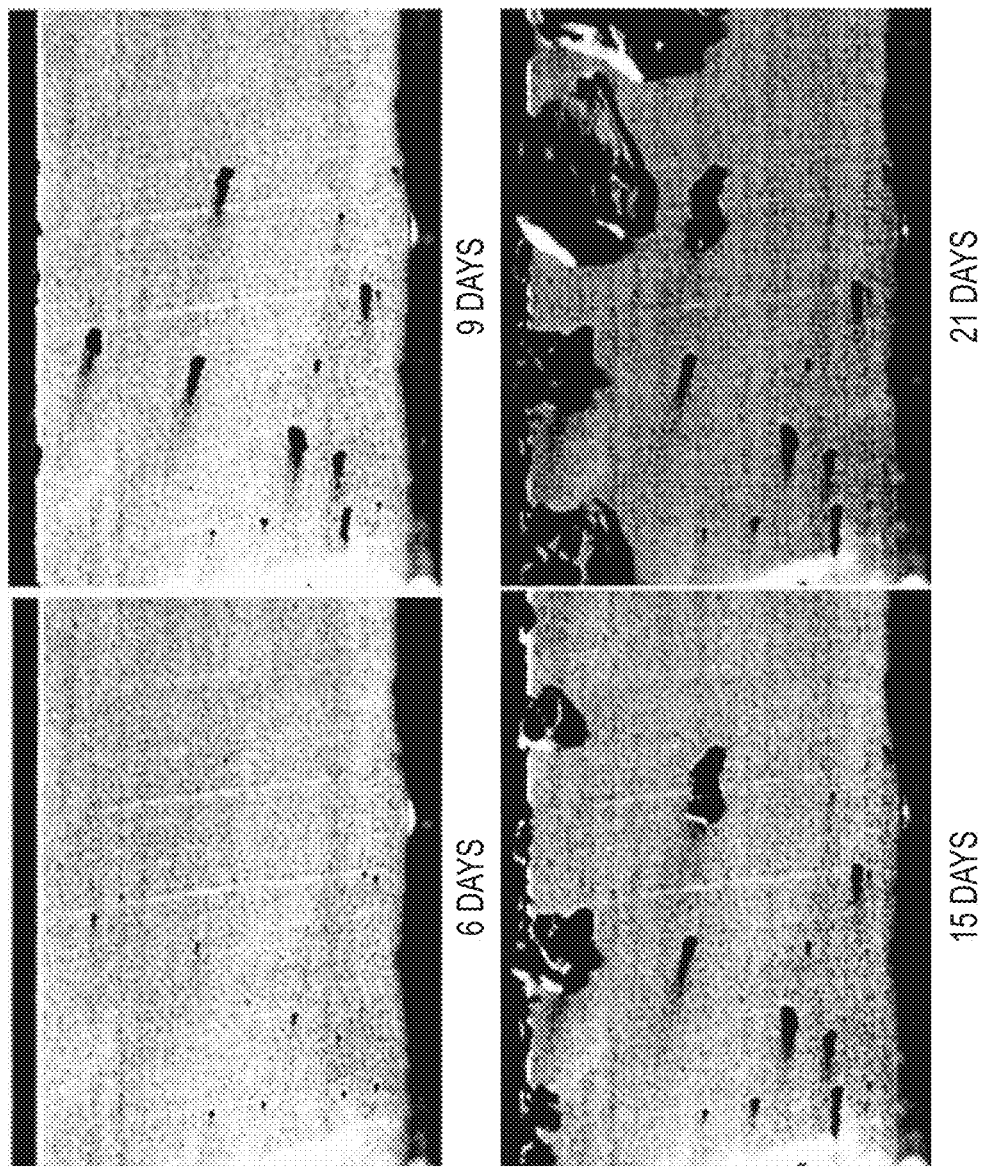
FIG. 7 shows examples of images, created while practicing a method described herein, of a substrate undergoing corrosion at four time intervals.

Creating the digital image can be acquired by simply taking a snap-shot of the substrate, and a series of digital images can be acquired by taking two or more snap-shots of the substrate over time. In certain embodiments, the digital images of the series of digital images are averaged, which can provide improved signal-to-noise ratio, as shown in FIG. 7, which, for example, may be used to create a time-lapse video synchronized to process data collected by measuring a parameter of the industrial water in the industrial water system. The method may further comprise analyzing (e.g., synthesizing) the data collected from the digital image, or series thereof, by mathematically transforming the data, which in certain embodiments may provide further insight on the detected corrosion. For the simple snapshot data collection shown in FIG. 7, a set of four images are shown covering a period of 21 days for a pretreated mild steel coupon. In this case, the coupon was exposed to water with the following composition (an example of industrial water, hereinafter "Water A"):

TABLE 1

The composition of Water A.

| Water A contents | Concentration (in ppm as $CaCO_3$) | Concentration (in ppm as the substance) |
|---|---|---|
| Calcium | 450 | 180 |
| Magnesium | 225 | 54 |
| Alkalinity | 100 | 122 |
| Chloride | 600 | 426 |
| Sulfate | 225 | 216 |

The Water A was treated with 100 ppm of a corrosion inhibitor comprising 4.5% ortho-phosphate, 4.5% phosphine succinc oligomer, 1.2% benzotriazole, 0.3% tolyltriazole, and 5.4% tagged high stress polymer (available from Nalco, an Ecolab Company, as 3DT189 corrosion inhibitor). Changes in the corrosion features on the coupon surface are clearly visible in the digital images of FIG. 7 as indicated by the dark areas against the coupon background. The size and appearance of new features is observed for the 21-day test. The ability to capture the coupon image at different times provides a means to monitor the changes occurring on the coupon surface, in this instance, due to corrosion. Furthermore, the ability to store image data provides the ability to compare current image data to past observations of different substrates of all kinds, e.g., similarly-situated substrates in the same industrial water system, similarly-situated substrates in different industrial water systems, statistical analyses of a population of substrates, and the like. For example, a series of digital images of a substrate can be created every 5, 10, 15 . . . days and analyzed against historical digital image data collected at the same incremental periods for one or more substrates located at the same position within the industrial water system. Observed differences between the data can indicate changes in the process due to the treatment program and/or water quality.

Utilizing digital image-processing algorithms can provide quantitative evaluation of the digital images, which provides quantitative evaluation of the corrosion of the substrate, and therefore of the corrosion of the industrial system. Data collected from the series of digital images can be used to develop overall trends related to a feature (or plurality thereof) or changes on the substrate surface area.

Figure 9:
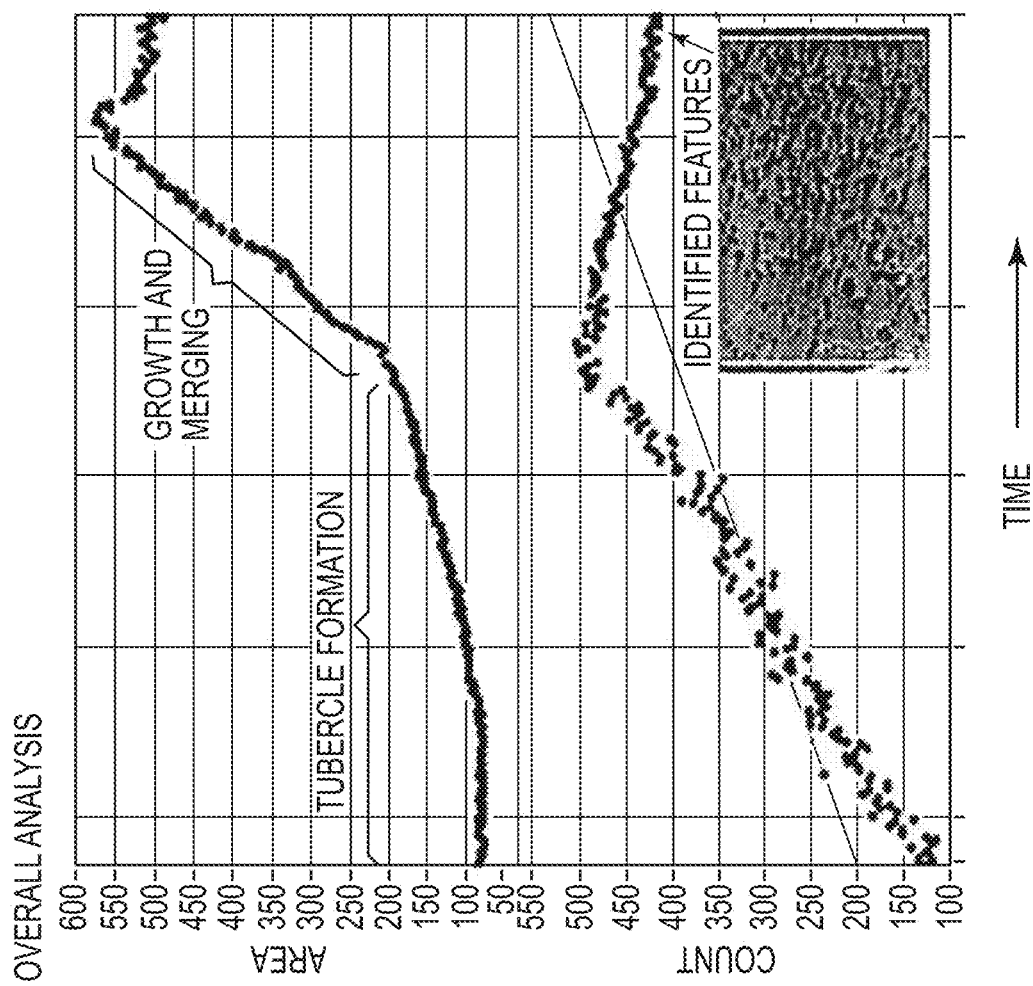
FIG. 9 shows an example of an image of a series of images subject to a method described herein.

An example outlining the steps to identify the number of corrosion features and average size is shown in FIG. 8. A region of interest is defined to limit the analysis of the series of digital images of the substrate. A threshold analysis is applied to identify corrosion features and reduce the N-bit image to a binary image, as shown in the lower left-hand quadrant of FIG. 8. from the binary image in FIG. 8, a clear distinction between the substrate where no corrosion activity is present (black background) and the corrosion features (white) can be observed. The surface areas of the corrosion features are calculated and binned to generate a distribution. From the distribution, general descriptive statics such as mean, standard deviation, range, etc., may be calculated and stored with the corresponding time stamp. Performing the steps on each image of a series of images allows for plotting the reduced data, e.g., as a trend plot for the average area and feature count (see, e.g., FIG. 9).

In certain embodiments, two-step threshold processing is applied (such as the one in the previous example) to identify the corrosion feature(s) involved. Two-step threshold processing made on each image accounts for variations in background and changes in the percent area coverage of the corrosion feature(s). The processing involves applying a coarse threshold to the digital image to locate corrosion features. For the previous example, the area of each feature from the coarse threshold is greater than the true area. Image masking is applied to the coarse threshold areas to remove the features from the image. An intensity histogram is calculated to determine the intensity distribution with no corrosion features, i.e., substrate background only. To determine the corrosion feature a fine threshold setting may be calculated using 3σ threshold values from the background distribution. For example, applying the calculated 3σ threshold values to the distribution in FIG. 8 using the 2-step threshold approach allows for identification of corrosion features. In certain embodiments, image processing methods using normalization and/or edge identification to detect sharp transitions between the background and corrosion feature(s) are used.

In certain embodiments, plotting variables such as percent area coverage and/or ratio of the average area divided by the number of features can also be created. Percent area coverage is based on the ratio of the overall corrosion feature area (sum of the area for all features identified) divided by the area of the region of interest. This provides a metric for the level of corrosion covering the surface.

The ratio of the average area divided by the number of features provides an indication on the type of corrosion, i.e., general versus localized. For example, two substrates with the same summed area of corrosion features is not descriptive regarding the type of corrosion. By including the feature count and developing a ratio of the summed area divided by the count, forms a new variable, which provides insight on the degree of localized corrosion. For this example, the substrate with the higher corrosion feature count would have a ratio value less than the case with fewer features indicating localized corrosion is more predominate.

Additional variables can be also be created by combining the corrosion data associated with the series of digital images with data obtained from corrosion monitoring probes, e.g., a Nalco corrosion monitoring (NCM) probe based on linear polarization resistance ("LPR"). LPR is a standard tool used for instantaneous general corrosion monitoring to trend the mils per year ("mpy") for different metallurgies. By analyzing data from a plurality of sources an estimated real-time localized corrosion rate and classification scheme for alarming can be created. For example, an alarming scheme developed following the data in Table 1 from Mars G. Fontana[5] (Corrosion Engineering, 3rd Edition) provides an example of classifying the level of localized corrosion. The data provides a starting point to develop an alarming scheme to alert users on the severity of localized corrosion and take proper corrective action early if needed. Additionally, the localized corrosion information correlated with events can be used as a troubleshooting tool. For example, for an industrial water system, an increase in localized corrosion after a make-up water change may indicate that the water quality is more corrosive than the previously used make-up water. Corrective action can be as simple as adding additional and/or a different corrosion inhibitor, or, in more severe cases, passing the make-up water through an ion-exchange column may be necessary to reduce the corrosivity of the make-up water.

TABLE 2

Localized corrosion rate classification for mild steel, all values are approximate.

| Relative corrosion resistance of common ferrous-and nickel-based alloys | mpy | mm/yr | μm/yr | nm/hr |
|---|---|---|---|---|
| Outstanding | <1 | <0.02 | <25 | <2 |
| Excellent | 1-5 | 0.02-0.1 | 25-100 | 2-10 |
| Good | 5-20 | 0.1-0.5 | 100-500 | 10-50 |
| Fair | 20-50 | 0.5-1 | 500-1000 | 50-150 |
| Poor | 50-200 | 1-5 | 1000-5000 | 150-500 |
| Unacceptable | >200 | >5 | >5000 | >500 |

Figure 10:
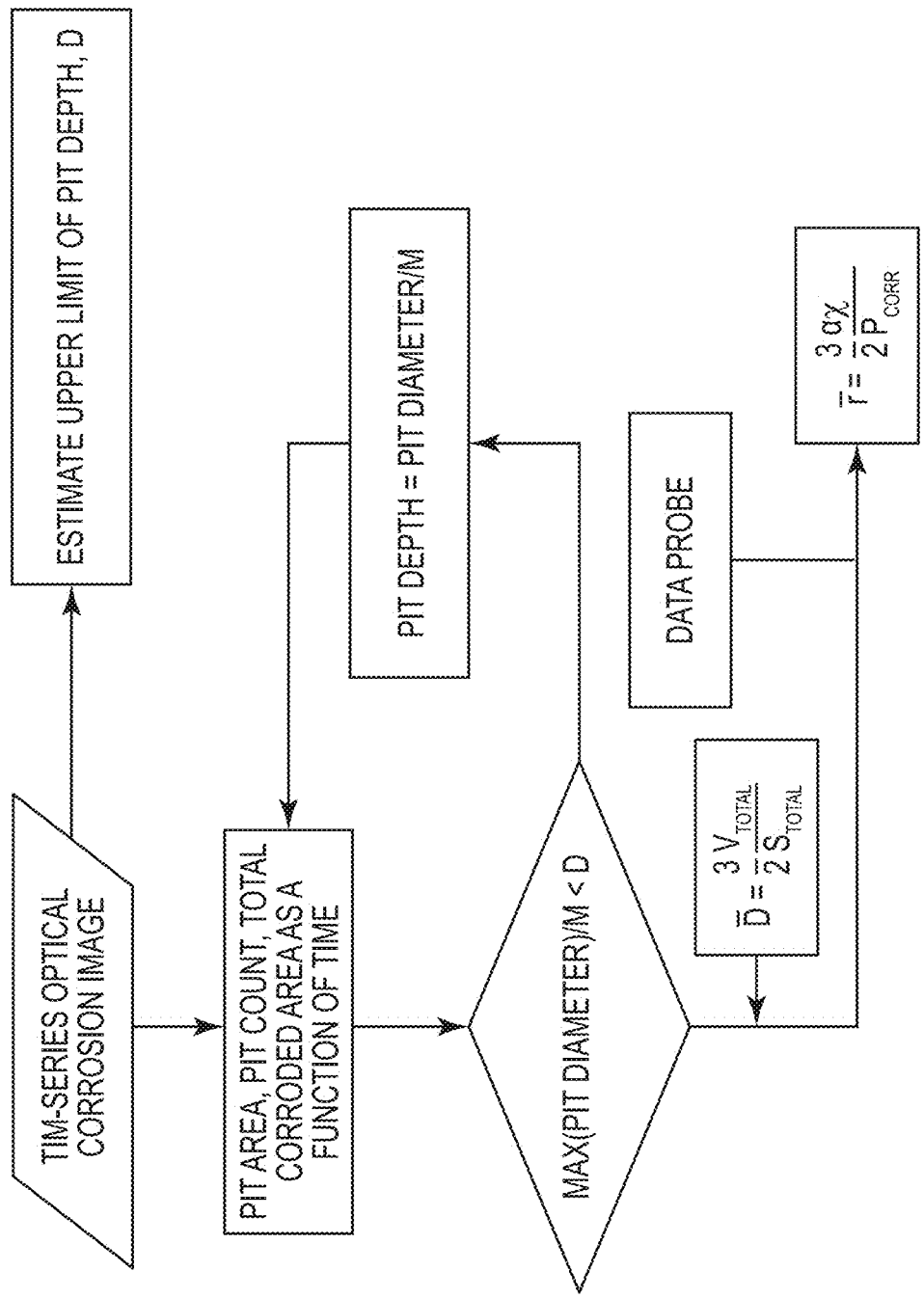
FIG. 10 is a flow chart of logic that is used in an embodiment of a method described herein.

For mild steel, corrosion pit depth estimation from analyzing the series of digital images follows the processing flow chart listed in FIG. 10. First, the upper limit pit depth is estimated assuming that once a pit is initiated it grows continuously with mass transport or diffusion as the rate-controlling factor. For a well-defined pit, this is believed to be the worst-case scenario. For pretreated mild steel coupons having double-ground finish, it was found that the upper limit pit depth can be estimated using the following mathematical transformation (Corrosion Science 50, 2008, 3193-3204):

$$d = 1.4 + 13.3 t^{0.5} \quad (1)$$

where t is expressed in days and the pit depth d in μm.

Substrate analysis from laboratory and field tests indicates the estimated upper limit pit depth d from Eq. (1) is always greater than the actual pit depth measurement. For coupons constructed of a different metallurgy and surface finish, an upper limit pit depth can be obtained empirically.

Furthermore, a heuristic calibration factor developed from offline substrate analysis, e.g., coupon removed from service and cleaned, shows that, for well-defined isolated pits (e.g., those having a sharp color change as compared to the background of the substrate), the pit equivalent diameter to depth ratio for metal coupons exposed to different conditions and durations is m:1, where m is from about 1 to about 30. Generally, the value of m depends on metallurgy, fluid flow conditions and corrosion inhibitor treatment conditions. For example, assuming typical conditions for a cooling water system, for mild steel coupons, m is about 5, and for admiralty brass coupons, m is about 15. Thus, the pit depth can be inferred from the pit area, except in the case where pits begin to overlap or large tubercles form due to underposit, which would result in much larger equivalent pit diameter than those of well-defined pits. The exception condition can be defined as maximum pit diameter divided by m larger than the upper limit pit depth. Alternative approaches for pit depth calculation are presented herein to address the exception.

Because corrosion 1) generally happens at n discrete pit regions with areas of $s_1, s_2, \ldots, s_n$, and depth of $d_1, d_2, \ldots, d_n$, the total area in the field of view of each digital image (which in certain embodiments makes up the region of interest) is $S_{fieldofview}$; and 2) generally results in pits that are hemisphere or semi-ellipsoidal in shape, the volume of each pit is equal to $\frac{2}{3} s_i d_i$, where i=1 to n. Thus, the averaged pit depth $\bar{d}$ weighted by pit areas can be expressed as the following mathematical transformation:

$$\bar{d} = \frac{\sum_{i=1}^{n} s_i d_i}{\sum_{i=1}^{n} s_i} = \frac{3}{2} \frac{\sum_{i=1}^{n} \frac{2}{3} s_i d_i}{\sum_{i=1}^{n} s_i} = \frac{3}{2} \frac{V_{total}}{S_{total}} \quad (2)$$

where $V_{total}$ is the total metal loss from the total area in the field of view and $S_{total}$ is the total corroded area in the total area of the field of view.

If the metal loss, $V_{total}$, is uniformly distributed in $S_{field\ of\ view}$, the depth is a general corrosion depth, $d_{general}$, can be calculated with the following mathematical transformation:

$$\bar{d} = \frac{3}{2} \frac{V_{total}}{S_{total}} = \frac{3}{2} \frac{d_{general} S_{field\ of\ view}}{S_{total}} = \frac{3}{2} \frac{d_{general}}{P_{corr}} \quad (3)$$

where $P_{corr}$ is percentage of corroded area in the field of view. According to Eq. (3), the average localized corrosion depth would be proportional to the reciprocal of percentage of corroded area.

Although $d_{general}$ is unknown, it can be calculated based on LPR data. The assumption is that the general corrosion depth, $d_{general}$, of a pretreated substrate is proportional to integrated LPR corrosion rate, $\chi$, times the total immersion time, t, according to the following mathematical transformation:

$$d_{general} = \alpha \chi t \quad (4)$$

where $\alpha$ is a calibration factor, $\chi$ is LPR general corrosion rate, and t is the total immersion time. Therefore, the average localized corrosion rate is obtained by combining Eq. (3) and (4) to obtain the mathematical transformation of Eq. (5):

$$\bar{r} = \frac{\bar{d}}{t} = \frac{3}{2} \frac{\alpha \chi}{P_{corr}} \quad (5)$$

where $\bar{r}$ is averaged localized corrosion rate, $\bar{d}$ is averaged pit depth weighted by pit areas, $\alpha$ is a calibration factor, i.e. a constant, $\chi$ is integrated LPR corrosion rate, t is the total immersion time, $P_{corr}$ is percentage of corroded area in the field of view.

Figure 11:
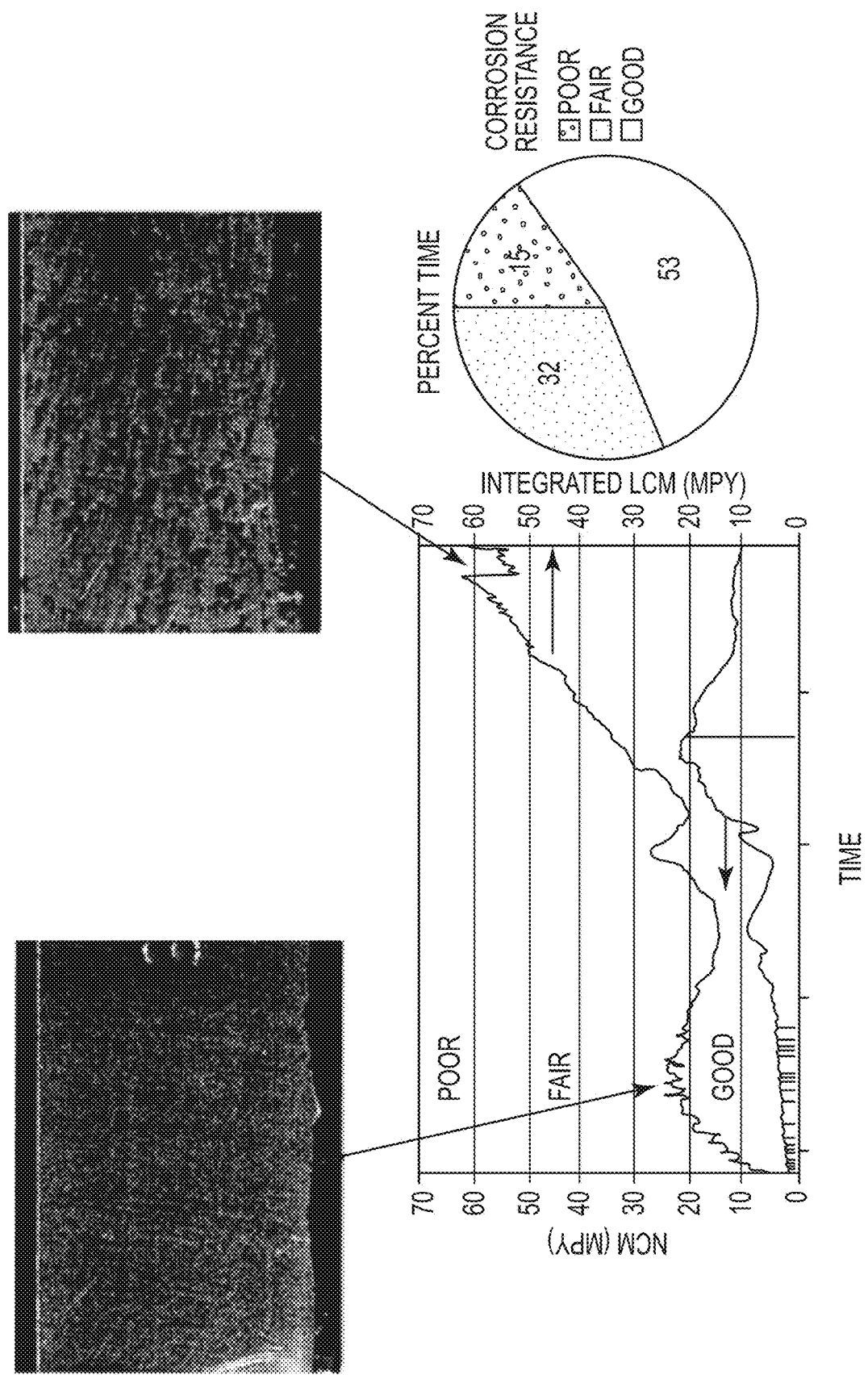
FIG. 11 shows examples of images subject to a method described herein.

An example using the above analysis is shown in FIG. 11 for LPR and digital imaging data collected on a mild steel coupon to estimate the integrated local corrosion value in mils per year. Changes in the corrosion features on the substrate surface are shown at different times. The alarm scheme developed to assess localized corrosion (i.e., localized corrosion measurement, or "LCM") according to the guidelines set forth in Table 1. During the first 10 days, the LCM remained low indicating good corrosion resistance with only a few minor excursions into the fair region. However, at a longer period the LCM continued upward into the poor corrosion resistance region. A breakdown of the percentage of time spent under the different corrosion resistance regions is also shown. This information provides a quick assessment on the treatment program effectiveness and identifies periods when corrosion control was poor and for how long. This example illustrates how the combination of digital imaging over time and LPR measurement can be used to alarm operators of the corrosion stress in the system and provide analysis for feedback control, which may comprise changing the dosing amount or treatment program. The example also illustrates a method to collect data dynamically and reduce the data to a trending variable for tracking, alarming and feedback control.

The integrated localized corrosion rate estimate provides an example of a mathematical transformation that yields an indication of the level of local and general corrosion. An additional or alternative approach uses the combination of digital imaging and LPR data based on the premise that corrosion is a slow process and detecting changes in the pit area and/or depth occurs gradually over time. For example, if the localized corrosion rate is, e.g., about 100 mpy (i.e., about 290 nm/hr), then the pit depth will take 16 hours to increase 4.6 μm. Using the heuristic ratio of 5:1 for pit diameter to depth, the pit diameter would increase 23 micron after 16 hours for this case, which is detectable by digital imaging. However, detecting instantaneous localized corrosion events based on image analysis alone is limited because of the gradual occurrence of corrosion over time.

A second approach is to extend the analysis to develop an instantaneous localized corrosion rate by differentiating Eq. (5) with respect to time to get the following mathematical transformation:

$$r = \frac{\partial \bar{d}}{\partial t} = \frac{\partial \left( \frac{3}{2} \frac{\alpha \chi t}{P_{corr}} \right)}{\partial t} = \frac{3}{2} \frac{\alpha}{P_{corr}} \frac{\partial \chi t}{\partial t} - \frac{3}{2} \frac{\alpha \chi t}{P_{corr}^2} \frac{\partial P_{corr}}{\partial t} = \frac{3}{2} \frac{\alpha}{P_{corr}} \delta - \frac{3}{2} \frac{\alpha \chi t}{P_{corr}^2} \frac{\partial P_{corr}}{\partial t} \quad (6)$$

where r is real-time localized corrosion rate, $\alpha$ is a calibration factor, i.e., a constant, $\delta$ is real-time LPR corrosion rate, $P_{corr}$ is percentage of corroded area in the field of view (e.g., region of interest). Generally, the area change for a pit occurs gradually, as a result change in $P_{corr}$ over a short time period is approximately zero, simplifying Eq. (6) to the following mathematical transformation:

$$r \approx \frac{3}{2} \frac{\alpha}{P_{corr}} \delta. \quad (7)$$

Here r is real-time average localized corrosion rate, $\alpha$ is a calibration factor, i.e., a constant, $\delta$ is real-time LPR corrosion rate, and $P_{corr}$ is percentage of corroded area in the field of view (e.g., region of interest).

Generally, given all factors being constant, pit depth growth rate is not constant: initially occurring at a faster rate and then plateauing over time. From Eq. (2) the pit depth is proportional to $t^{0.5}$, i.e., $$d \propto t^{0.5} \text{ and} \quad (8)$$

$$\frac{\partial d}{\partial t} \propto t^{-0.5} \text{ thus,} \quad (9)$$

$$r \propto t^{-0.5}, \quad (10)$$

each of which is a mathematical transformation, where d is pit depth, r is real-time average localized corrosion rate and t is the total immersion time. Therefore, the projected corrosion rate after three months service can be obtained based on a shorter time treatment using Eq. (10). For example, the ratio of the projected real-time average localized corrosion rate after three month (30-day months) treatment to the real-time average localized corrosion rate at time t can be expressed as the following mathematical transformation:

$$\frac{r_{projected}}{r} = \frac{90^{-0.5}}{t^{-0.5}} = \frac{t^{0.5}}{90^{0.5}}. \quad (11)$$

Using Eq. (11), the corrosion rate of 100 mpy after three days treatment is equivalent to 18 mpy after 90 days. Eq. (11) can be combined with Eq. (7) to give the following mathematical transformation:

$$r_{projected} \approx \frac{3}{2} \frac{\alpha}{P_{corr}} \delta \frac{t^{0.5}}{90^{0.5}} \quad (12)$$

where $r_{projected}$ is a normalized real-time average localized corrosion rate for 90 days, $\alpha$ is a calibration factor, i.e., a constant, $\delta$ is real-time LPR corrosion rate, $P_{corr}$ is percentage of corroded area in the field of view, and t is total immersion time.

Figure 12:
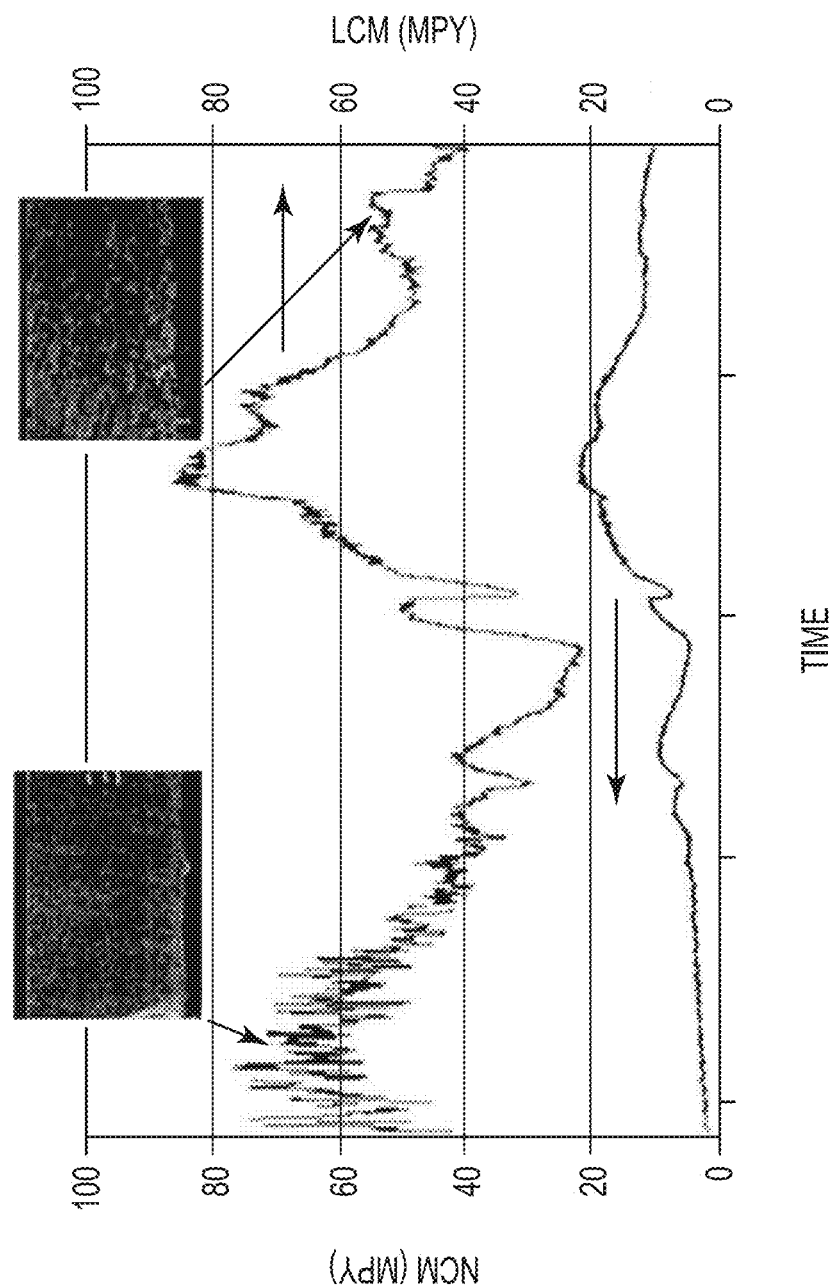
FIG. 12 shows examples of images subject to a method disclosed herein.

An example applying the concept of a normalized real-time average localized corrosion rate is shown in FIG. 12 along with data from the standard LPR measurement from FIG. 11 data. In FIG. 12, the combination of imaging data and LPR has been used to rescale the data to reflect the localized corrosion activity. The initial normalized LCM result is greater than 60 mpy with a Nalco Corrosion Monitor ("NCM") reading<2 mpy indicating that localized corrosion is dominating consistent with the digital image data that shows only a few very small active sites. As time progresses, the number of corrosion sites identified by digital imaging analysis increases and the normalized LCM and LPR values are approximately 55 mpy and approximately 10 mpy respectively. This suggests that the density of corrosion features is relatively high, e.g., area coverage approximately 10%, indicating that both localized and general corrosion are present.

Figure 13:
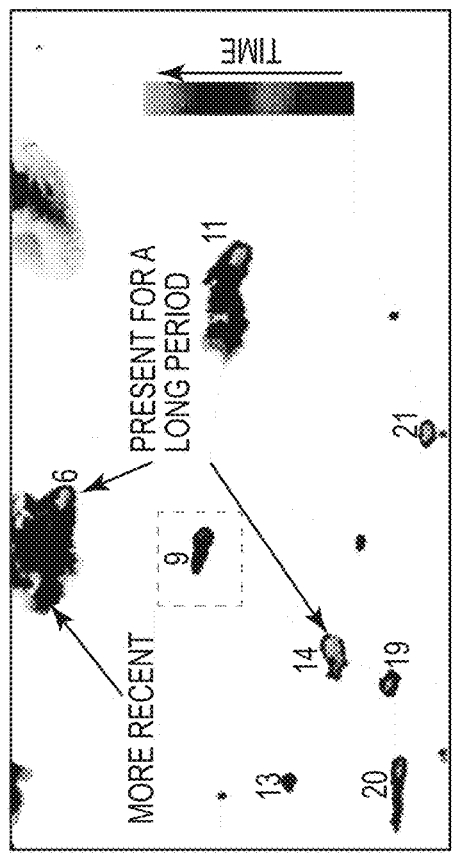
FIG. 13 shows an example of an image of a series of images subject to a method described herein.
Figure 14:
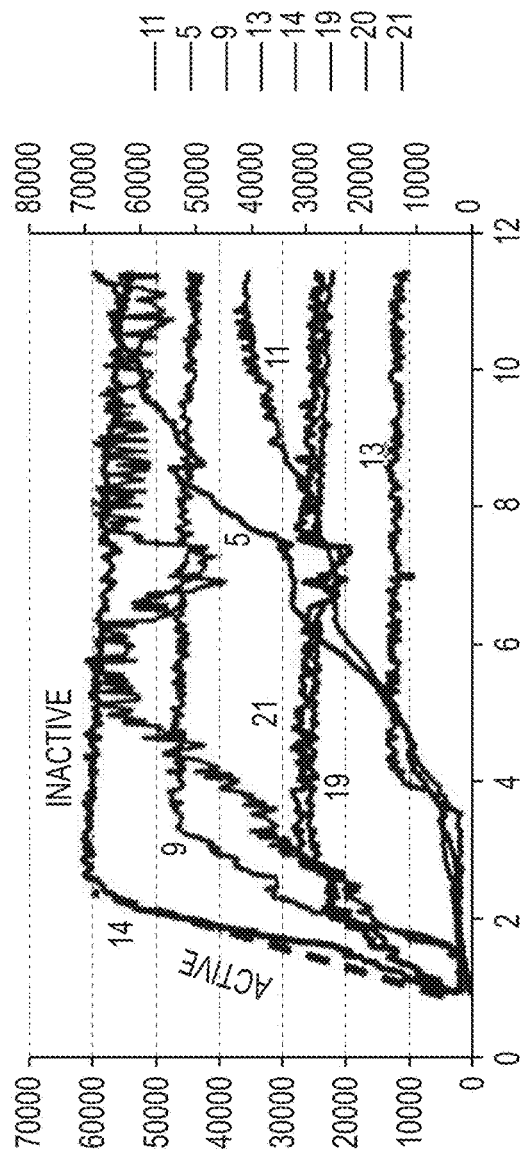
FIG. 14 is a graphical illustration of a property of certain corrosion pits present in the image of FIG. 13.
Figure 15:
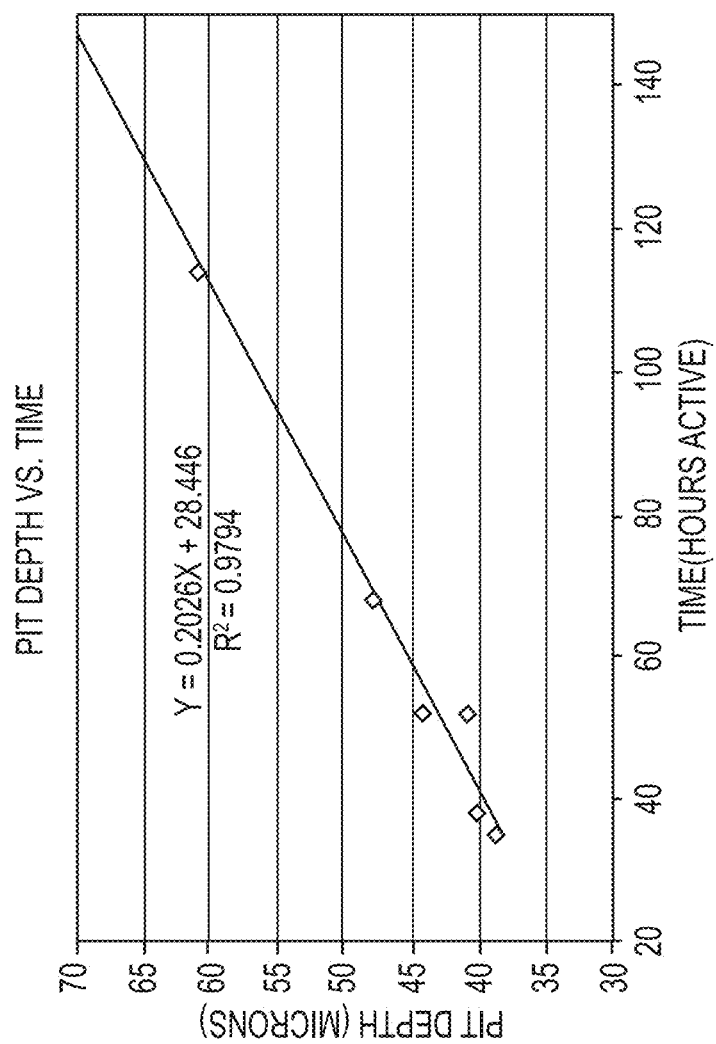
FIG. 15 is a chart of corrosion pit depth versus time for certain experiments performed on a certain type of substrate.

A further aspect of the methods set forth herein is to track the corrosion surface area change and integrated time for individual corrosion features. Using digital imaging analysis in combination with other sensor data, e.g., pH, conductivity, ORP, LPR, etc., can allow for shortening of evaluation time for a corrosion treatment program. In certain circumstances, limited experimental evidence may suggest that pit depth estimation or corrosion rate can be obtained much sooner than the typical substrate service period where information is obtained only after the substrate (e.g., coupon) is removed from service. An example supporting this finding is shown in FIGS. 13-15, where individual tubercles are identified and tracked over time. FIG. 13 shows a normalized time averaged tubercle features captured by digital imaging after approximately 15 days exposure to Water A treated with 100 ppm 3DT189. The gray scale is normalized to the total coupon immersion time. For example, the light-shaded area indicates the feature has been present the longest whereas appearance of the darker color is more recent, as indicated by FIG. 13. The light dark color is an indication of the corrosion feature, i.e., tubercle area, is actively expanding. By using the time averaged area image, identification and number of active tubercles can be quickly located. FIG. 14 shows the area change for each tubercle corresponding to the labeled feature in FIG. 13. For example, for the tubercle labeled 14, the normalized time averaged area in FIG. 13 is light colored indicating little if any change in area occurred for a large portion of the total coupon immersion time. In contrast, the time averaged area for tubercles labeled 5 and 11 appear very active. The light areas for these tubercles show where the initiation point started with the actively changing area appearing dark.

In certain embodiments, the analyzing of the series of digital images comprises analyzing (e.g., synthesizing) dynamic activity of a tubercle in the region of interest. Using the same set of tubercles identified in FIG. 13 the growth profile for each tubercle is plotted in FIG. 14. The data shows rapid area growth for all tubercles except 5 and 11 over a relatively short period before reaching a plateau. If the plateau region is considered inactive, a plot of the active time from FIG. 14 exhibits a good correlation with the offline pit depth measurement from a substrate (e.g., coupon). In this case, the digital imaging analysis would track the area change for isolated individual tubercles to identify the active period and extrapolate a pit depth based on the calibration curve shown in FIG. 15. This analysis provides the ability to project pit depth or corrosion rate three months later based on corrosion data collected over a much shorter period.

In certain embodiments, the methods disclosed herein provide the ability to identify corrosion sites, including active corrosion sites, based on color analysis and classification. For example, mild steel corrosion is known to form tubercles comprising mounds of corrosion products. The color of these products generally provides some insight on the mound structure. Hematite is generally reddish brown to orange in appearance while magnetite generally appears blackish. The color can provide information related to whether a corrosion feature may be aggressive. Generally, for mild steel, a highly aggressive corrosion site color tends to be more orange-red in appearance. In some cases, a color change can be detectable with the addition of an inhibitor causing the color to appear darker. Using a color digital imaging device, the image collected can be associated with the red-green-blue ("RGB") color model. These individual color planes can be extracted to view and process as well as convert to other color models such as hue, saturation, intensity ("HSI"), which corresponds closely to how the human eye interprets color. An example illustrating the change in color with the addition of an inhibitor is shown in FIG. 16 for a mild steel coupon exposed to Water A for 24 hours then treated with an inhibitor (in this instance, 3DT189 as described herein).

Figure 17:
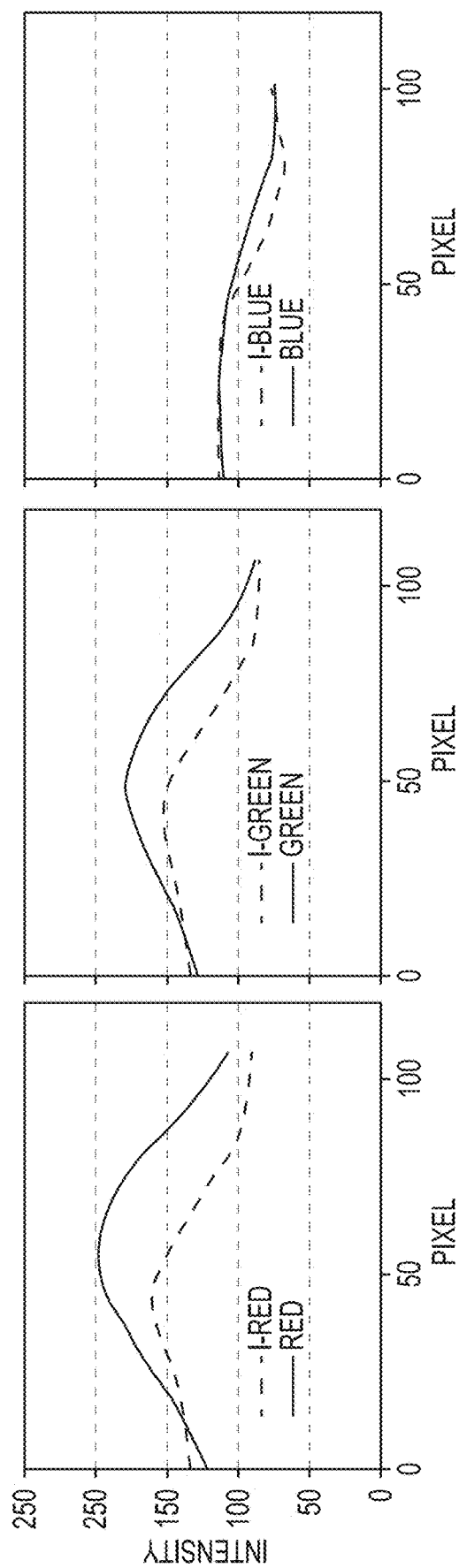
FIG. 17 shows charts of embodiments reflecting analyses of a series of digital images, one each for red, green and blue light reflectance.

The image shown in FIG. 16 represent the extracted red plane. The overall intensity of the corrosion features is higher for the non-inhibited case compared to same coupon after addition of inhibitor. The difference is subtle but becomes clearer by binning the line profile intensity for the selected region of interest for each color plane. The averaged bin values are the sum of the line profiles divided by the number of profiles. The results for red, green, and blue are shown in FIG. 17. The dashed profiles are the cases with inhibitor added. In addition to the overall size not changing after addition of the inhibitor, a significant decrease in the red and green intensity occurs indicating a decrease in corrosion activity. This change in color is a discriminating factor to identify local active versus inactive corrosion sites.

Figure 18:
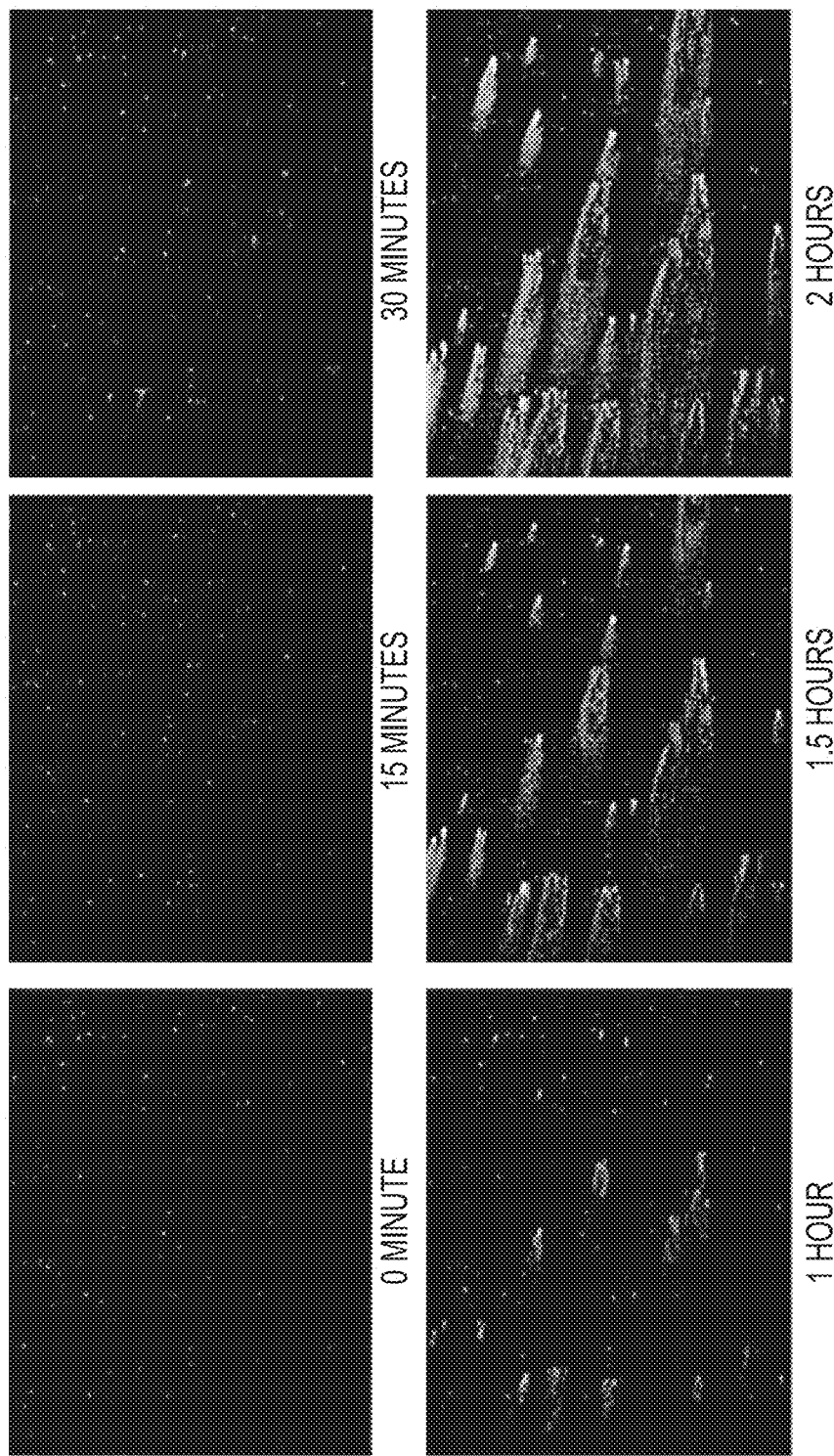
FIG. 18 shows examples of images, created while practicing a method described herein, of a substrate undergoing corrosion at six time intervals.

In certain embodiments, the methods disclosed herein can be utilized to evaluate corrosion properties via accelerated corrosion. As discussed, pit initiation and pit growth in the presence of a corrosion inhibitor is generally a slow process, routinely taking 3 days or more to generate pits, and additional two weeks or longer to differentiate pit growth changes with a corrosion inhibitor program. An example of a mild steel substrate showing pit initiation and growth is shown in FIG. 18 for a series of digital images collected. In the absence of corrosion inhibitor, pit initiation occurred within 30 minutes. By controlling the time duration of the substrate contacting industrial water in the industrial water system, pit size of the corrosion features is also controlled. Once the desired pit size is achieved, a corrosion inhibitor can be added to reduce or quench the corrosion (area and/or pit) rate. The approach of initiating a desired pit size followed by adding inhibitor can accelerate the evaluation process for the overall effectiveness of a corrosion inhibitor program.

In certain embodiments, the methods further comprise enhancing corrosion features in the region of interest via adding a fluorescing moiety to the industrial water in the industrial water system. By adding a fluorescing moiety to the industrial water, the fluorescing moiety attaches or reacts with the corrosion features. Detection can be made by using an excitation illumination source at the appropriate wavelength. Light emission can be captured by the imaging device to provide a 2D map of the fluorescence originating from the corrosion features of the substrate surface.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. In particular, the word "series" appears in this application and should be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of analyzing a substrate contacting fluid present in an industrial system, the method comprising:
   creating a digital image of the substrate while the substrate contacts the fluid present in the industrial system;
   defining a region of interest in the digital image of the substrate;
   identifying a corrosion feature in the region of interest in the digital image of the substrate; and
   analyzing the corrosion feature in the region of interest in the digital image of the substrate.

2. The method of claim 1, further comprising moving the substrate in the industrial system to expose a second region of interest to digital imaging; and repeating the steps of the method.

3. The method of claim 1, wherein the fluid is industrial water and the industrial system is an industrial water system.

4. A method of analyzing a substrate contacting fluid present in an industrial system, the method comprising:
   creating a series of digital images of the substrate while the substrate contacts the fluid present in the industrial system;
   defining a region of interest in the series of digital images of the substrate;
   identifying a corrosion feature in the region of interest in the series of digital images of the substrate; and
   analyzing the corrosion feature in the region of interest in the series of digital images of the substrate to determine a corrosion trend of the industrial system.

5. A method of analyzing a substrate contacting industrial water present in an industrial water system, the method comprising:
   treating the industrial water of the industrial water system with a corrosion inhibitor;
   creating a series of digital images of the substrate while the substrate contacts the industrial water present in the industrial water system;
   defining a region of interest in the series of digital images of the substrate;
   identifying a corrosion feature in the region of interest in the series of digital images of the substrate;
   analyzing the corrosion feature in the region of interest in the series of digital images of the substrate to determine a corrosion trend of the industrial water system; and
   acting based on the analysis of the corrosion feature in the region of interest in the series of digital images of the substrate.

6. The method of claim 5, further comprising measuring a parameter of the industrial water present in the industrial water system selected from pH, conductivity, oxidation-reduction potential, linear polarization resistance, derivatives thereof, and combinations thereof.

7. The method of claim 5, further comprising estimating the surface area of the corrosion feature.

8. The method of claim 7, further comprising estimating pit depth of the corrosion feature based on the estimated surface area of the corrosion feature.

9. The method of claim 7, further comprising estimating pit depth of the corrosion feature based on a one-dimensional measurement of the corrosion feature.

10. The method of claim 5, further comprising identifying a plurality of corrosion features in the region of interest.

11. The method of claim 10, further comprising counting the plurality of corrosion features.

12. The method of claim 10, further comprising counting and tracking the plurality of corrosion features.

13. The method of claim 5, wherein the substrate is a corrosion coupon.

14. The method of claim 13, wherein the corrosion coupon is capable of undergoing an ASTM corrosion test.

15. The method of claim 13, wherein the corrosion coupon is constructed of a metal selected from steel, iron, aluminum, copper, brass, nickel, and related alloys.

16. The method of claim 15, wherein the metal is steel selected from mild steel, stainless steel, carbon steel, and related alloys.

17. The method of claim 16, wherein the steel is mild steel.

18. The method of claim 5, wherein the acting comprises at least one of increasing dosage of corrosion inhibitor, selecting a different corrosion inhibitor, modifying the corrosion inhibitor, altering a physical property of the industrial water system, and shutting down the industrial water system.

19. The method of claim 5, wherein the analyzing of the corrosion feature of the region of interest of the series of digital images comprises classifying corrosion on the substrate according to color profile of the region of interest or subregion thereof of at least one of the series of digital images.

20. The method of claim 5, further comprising moving the substrate in the industrial system to expose a second region of interest to digital imaging; and repeating the steps of the method.

* * * * *